(12) United States Patent
Deutschmann

(10) Patent No.: US 8,340,460 B2
(45) Date of Patent: Dec. 25, 2012

(54) ESTIMATING AN OFFSET IMAGE OF A NEW IMAGING DEVICE FROM THE OFFSET IMAGE OF AN AGED IMAGING DEVICE

(76) Inventor: Heinz Deutschmann, Salzburg (AT)

(*) Notice: Subject to any disclaimer, the term of this patent is extended or adjusted under 35 U.S.C. 154(b) by 966 days.

(21) Appl. No.: 12/288,358

(22) Filed: Oct. 17, 2008

(65) Prior Publication Data

US 2009/0129659 A1  May 21, 2009

(30) Foreign Application Priority Data

Oct. 18, 2007  (EP) .................................... 07118784

(51) Int. Cl.
*G06K 9/40* (2006.01)
(52) U.S. Cl. ....................................................... 382/275
(58) Field of Classification Search .................. 382/275
See application file for complete search history.

(56) References Cited

U.S. PATENT DOCUMENTS

| | | | |
|---|---|---|---|
| 5,444,756 A | | 8/1995 | Pai et al. |
| 5,737,251 A | * | 4/1998 | Kohno et al. ............... 708/207 |
| 6,012,640 A | * | 1/2000 | Liu .......................... 235/462.25 |
| 6,122,016 A | | 9/2000 | De Haan et al. |
| 6,965,395 B1 | * | 11/2005 | Neter ........................... 348/129 |
| 7,075,061 B2 | | 7/2006 | Spahn |
| 7,224,770 B2 | | 5/2007 | Spahn |
| 7,239,743 B2 | * | 7/2007 | Gardella et al. ............. 382/166 |
| 2003/0072418 A1 | | 4/2003 | Albagli et al. |
| 2003/0169850 A1 | | 9/2003 | Kump et al. |
| 2004/0156542 A1 | * | 8/2004 | Barone et al. ................ 382/166 |
| 2005/0151086 A1 | | 7/2005 | Spahn |
| 2005/0282175 A1 | * | 12/2005 | Taylor et al. ..................... 435/6 |
| 2006/0237671 A1 | | 10/2006 | Shoji |
| 2007/0183682 A1 | * | 8/2007 | Weiss ............................ 382/261 |

FOREIGN PATENT DOCUMENTS

| | | |
|---|---|---|
| DE | 103 34 395 | 3/2005 |
| DE | 103 43 787 | 4/2005 |
| EP | 0 817 210 | 1/1998 |
| WO | WO 00/65374 | 11/2000 |
| WO | WO 2006/001782 | 1/2006 |

OTHER PUBLICATIONS

Reddy P. et al., "Reference Free Nonuniformity Correction for Mercury Cadmium Telluride Infrared Focal Plane Arrays," Communications and Signal Processing, Proceedings of the 1998 South African Symposium on Rondebosch, IEEE, pp. 243-248, 1998.
Chapuy, S. et al., "Optimization of a high resolution real-time solid state X-ray detection system for mammography," Proc. of SPIE, vol. 5199, pp. 173-180, Mar. 2004.
Roberts, D.A. et al., "Charge Trapping at High Doses in an Active Matrix Flat Panel Dosimeter," IEEE Transactions on Nuclear Science, vol. 51, No. 4, pp. 1427-1433, Aug. 2004.
Irsigler, R. et al., "320×240 GaAs pixel detectors with improved X-ray imaging quality," Nuclear Instruments & Methods in Physics Research A 460, pp. 67-71, 2001.
Moran, J.M. et al., "An Active Matrix Flat Panel Dosimeter (AMFPD) for in-phantom dosimetric measurements," Med. Phys. 32 (2), pp. 466-472, Feb. 2005.

* cited by examiner

*Primary Examiner* — David Zarka
(74) *Attorney, Agent, or Firm* — Kagan Binder, PLLC

(57) ABSTRACT

The present invention relates to methods and systems for improving image quality of imaging devices such as image detectors, and preferably of flat panel detectors such as amorphous silicon flat panel detectors, for example used in radiotherapy. The invention also relates to the improving of life span of used or aged detectors.

5 Claims, 23 Drawing Sheets a b

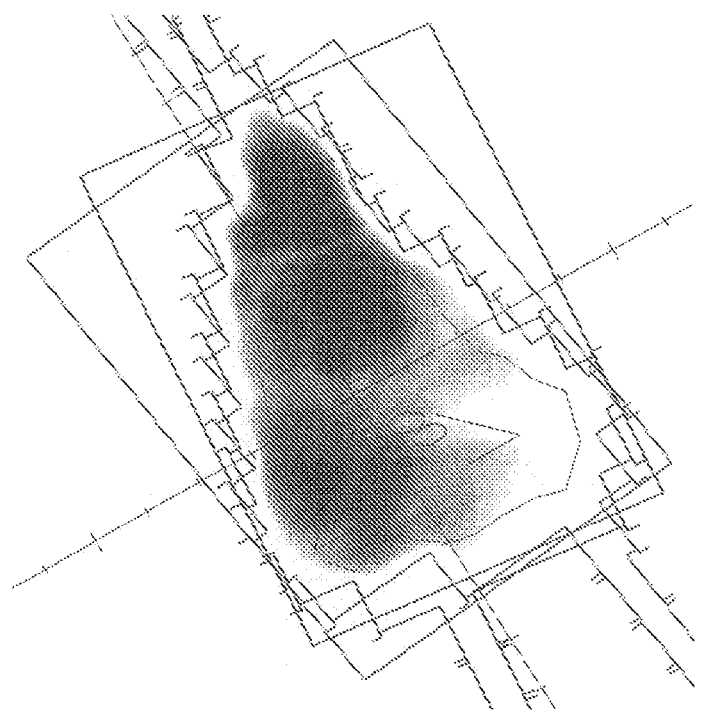
Fig. 20
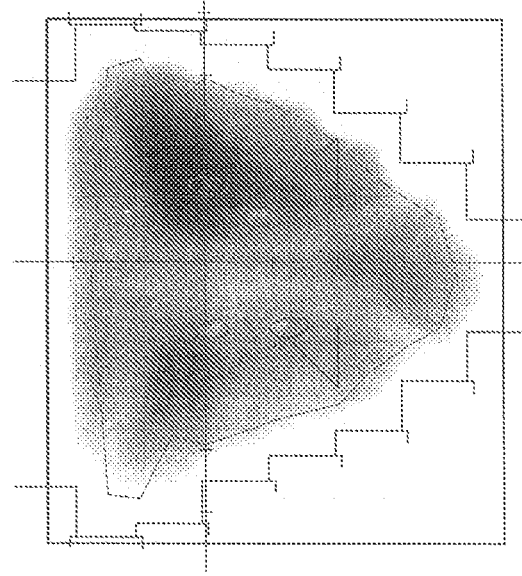

ESTIMATING AN OFFSET IMAGE OF A NEW IMAGING DEVICE FROM THE OFFSET IMAGE OF AN AGED IMAGING DEVICE

PRIORITY

The present patent Application claims priority from European Application No. 07118784.3 which was filed on Oct. 18, 2007, the entirety of which is incorporated herein by reference.

TECHNICAL FIELD

The present invention relates to methods and systems for improving image quality of imaging devices such as flat panel detectors like amorphous silicon (aSi:H) flat panels, for example used in radiotherapy. The invention also relates to the improving of life span of used or aged detectors.

BACKGROUND OF THE INVENTION

Many types of digital imaging devices create image data using stored electrical charge. For example, known charge-coupled devices (CCDs) convert light to electrical charge and store the electrical charge for subsequent readout. In the case of amorphous silicon devices, a scintillating layer receives X-rays and generates light in proportion to the intensity of the received X-rays. An array of amorphous silicon photodiodes then converts and stores the generated light as electrical charge. For example, a photodiode of an amorphous silicon flat panel accumulates charge in proportion to an intensity of light received from an associated radiation source. After a specified time period, the accumulated charge is read in order to calculate the intensity of an image pixel associated with the photodiode. Accordingly, the accumulated charge is preferably directly proportional to the received light.

However, the photodiodes of the amorphous silicon sensors require a small bias voltage for proper operation. This bias voltage generates a small "dark current" that may cause a charge to accumulate within the photodiode that is unrelated to the intensity of the received light. This dark current thereby causes errors in the calculated intensity of the associated image pixel. Other imaging devices that convert radiation to electrical charge suffer from similar dark current problems.

Digital imaging devices as used in radiology or radiotherapy are typically flat panel imaging devices with amorphous silicon sensors deployed in a two-dimensional array. Such amorphous silicon (aSi:H) flat panel detectors are for example used as electronic portal imaging devices (EPID) on linear accelerators to a) image patient's anatomy or test phantoms and verify beam's aperture with high energy megavoltage (MV) beams delivered for treatment in radiotherapy, either in still planar views or in video mode (online) or in three-dimensional (3D) cone beam (CB) reconstructions, b) measure doserates or doses absolutely and relatively for machine quality assurance (maintenance, calibration of beam limiting and delivering devices) and in vivo (back projection to derive delivered dose distributions within a patient), or c) image patients' anatomy or test phantoms with kV beams delivered from an additional X-ray source to enable 2D, 3D and 4D (time-dependant) analysis.

In radiotherapy, aSi:H flat panels are widely used routinely for daily verification of patient's setup, and image quality and stability is of increasing relevance in the upcoming field of adapted image guided radiotherapy (IGRT) techniques. Typically, a MV panel on a standard linear accelerator (linac) has to capture images of several beams per patient every 10 to 15 min under very different conditions (anatomy, doserate, monitor units, beam energy, temperature). Since the device is irradiated with high energy photon beams, scattered dose (and occasionally the primary beam) damages the electronic components of the readout system (amplifiers) of the panel, so that the average life span of a clinically useable panel under such conditions may often not exceed 18 months.

Several approaches have been taken in an attempt to address the foregoing problems. One approach applies image processing techniques to each image frame that is produced from electrical charges read from an array of imaging elements. Known as offset correction, this approach involves acquiring image frames during a period of non-irradiation, calculating an average image frame from the acquired frames, and subtracting the average image frame from each frame acquired during subsequent radiation of the imaging elements. The averaged image frames are preferably acquired at the same rate as the subsequently-acquired frames so as to better approximate the effect of dark current on the subsequently-acquired frames. Since the extent of dark current effects varies across imaging devices, imaging devices are often sold with customized software for performing offset correction.

Furthermore, a linear relationship between doserate (or dose per frame) and pixel signal is conventionally assumed to achieve clinically useful images, which is roughly correct for newer panels. Although non-linear effects are known, the change of gain is relatively small at all higher doserates so that a fairly linear behaviour is assumed. Therefore, many sites in clinical and research environments found a sole background (or offset) and a linear gain correction to be sufficient, even if the panel was used for dosimetric purposes. A gain image describes a constant (linear) slope, which is assumed to be the pixel sensitivity. Conventional panel applications provide methods to acquire and store the gain image for a specific panel. For this purpose, the panel has to be irradiated with a flood field at a constant, higher doserate. The gain can simply be derived by dividing the doserate (normalized to a 16 bit value lower than or equal to hFFFF=65535) by the signal that has previously to be reduced by a provided offset value. Basically, this describes a two point measurement (background at doserate 0 and flood field at a high doserate), and considers linearity in between. Gain images were found to be relatively stable in time. For this reason, it is quite often decided to never recalibrate the gain during the life span of a panel.

However, offset correction, gain correction or recalibration often fails to provide suitable improvements with respect to image quality and life span of aged panels. Additional or alternative methods and systems are therefore desirable.

SUMMARY OF THE INVENTION

The present invention relates to methods and systems for improving image quality of imaging devices such as flat panel detectors like amorphous silicon (aSi:H) flat panel detectors, for example used in radiotherapy.

A radiation therapy system according to the present invention preferably comprises one or more radiation sources or radiation systems, for example an electron radiation source or a photon radiation source and an additional X-ray source. The radiation sources each preferably direct a beam of radiation along a beam path toward a volume to be irradiated. In a preferred embodiment, one radiation source is a linear accelerator's head emitting radiation in the megavolt-range (MV) for therapy and a second is an X-ray source, emitting radiation at energies in the kilovolt (kV) range. The radiation therapy system preferably further comprises a treatment couch for the patient, one or more imaging devices, and an operator station. The treatment head includes a beam-shielding device, or collimator for shaping the beam and for shielding sensitive areas from the beam. Moreover, the treatment head comprises a monitor chamber to measure the quantity of emitted radiation. The beam may comprise electrons, photons or any other type of detectable radiation.

The imaging devices are preferably an electronic portal imaging device (EPID) to image the MV beam and an additional panel to image the kV beam, both preferably flat panel detectors. In more detail, the imaging devices are used to acquire images of an internal portion of patient for adaption, verification and recordation of the patient's setup and/or a treatment field's aperture. Since the acquired images are used to determine conformance with a treatment plan, accuracy of the images is crucial. Cure rates for many tumors are a sensitive function of the radiation dose they receive, so treatment plans are designed to maximize radiation delivered to a target while minimizing radiation delivered to healthy tissue and organs nearby. Modern treatment plans require fine control of beam shape and patient positioning in order to achieve these goals.

The imaging device is preferably an amorphous silicon flat panel with sensors deployed in a two-dimensional array. The XRD 1640 series, offered by PerkinElmer®, Inc. of Fremont, Calif., is one suitable device series. The sensors of the imaging device record the intensity of received light as stored electrical charge, and may be read to capture an image frame. The captured image frames are then corrected to create an image of the radiation field, thereby allowing quick and efficient verification of the treatment field including patient anatomy, patient position and beam shape.

A first aspect of the invention relates to the fact that the background (or offset) images on older panels show disturbingly grouped horizontal lines (rows), known as COB artifacts. Typically, a panel used as an imaging device comprises a plurality of rectangular sub-panels (for example 2×8 sub-panels), and the disturbing lines can be found parallel to the long sides of each sub-panel. This phenomenon is described below in more detail with reference to the drawings. It was found that, when a detector is aging, the background signal for all pixels in some of these rows increases from relatively low values on new panels up to the double or more on older panels. This is due to the fact that panel destruction may be caused by the damage of the amplifiers of the readout system, which addresses a pixel in the image by row and column. The disturbing stripes in the offset image are usually not predominant on new panels. The rest of information in the offset image (texture patterns that stem from manufacturing processes) is roughly the same in old and in new panels. Thus, a subtraction of the offset image of the new panel from the offset image of the aged panel would separate the row specific component from the native (i.e. uncorrected) offset image. However, this is not possible if the offset image of the new panel is not available, for example if it was not taken and stored at the time of first use of the panel.

Therefore, according to the first aspect, the invention provides a method of separating the row specific component from the native (i.e. uncorrected) offset image in absence of the offset image of the new panel. Accordingly, first the median value of all pixels in each row of each sub panel is calculated. Assuming that the minimum value of all medians of all sub panel rows of the panel is the corresponding value for a new panel, the difference between each row's median and the minimum sub panel row median of the panel is calculated in the next step and set to be the disturbing/noisy part of the aged panels offset image, whereas the remaining pixel value is the corresponding value of that pixel in the original, new panel.

Thus, the invention provides a method of estimating an offset image of a new imaging device from the offset image of said imaging device already aged, comprising the steps of (a) calculating the median offset value of all pixels in each sub-panel's row of an aged imaging device; (b) determining the minimum value of all medians of all rows of the aged imaging device; (c) setting the minimum value of all medians of all rows of the aged imaging device as the estimated offset image of the unused imaging device.

The invention further provides a method of image correction comprising the steps of (a) calculating the median value of all pixels in each row of an aged imaging device; (b) determining the minimum value of all medians of all rows of the aged imaging device; (c) calculating for each row the difference between the median value of each row and the minimum value of all medians; (d) setting the difference as the disturbing part of the aged offset image; and (e) subtracting the difference from a target image obtained with the aged imaging device.

More accurately, it was found that the remaining signal variations of offset image pixel intensity values along sub-panel rows differ from row to row. The lower the row's median value, the higher the remaining variations. Poor rows in aged panels with relatively high medians show little variations.

Thus, the invention further provides a method of increasing the low signal variations along poor subpanel rows in aged panels by (a) calculating the standard deviations of pixel intensity values along all subpanel rows; (b) deriving the quotient of the standard deviation of the $n^{th}$ row and the standard deviation of the best row, which is assumed to be the row with the lowest median; (c) setting the pixel value in the corrected offset image to the intensity given by dividing its original difference to the row's median with the quotient derived in (b) and adding this to the row's median. The resulting image shows a uniformly distributed high frequency texture but no line artifacts, and is named the "clean" offset image in further explanations.

Alternatively, the separation of the offset images of an aged imaging device from the offset image of the unused imaging device can be performed directly in the frequency domain, for example by using a Fast Fourier transformation.

The separation or offset image estimation, respectively, according to the first aspect of the invention is, according to the second aspect of the invention, also applied on gain images. This would ideally require that the gain image is acquired by irradiation with a perfectly homogeneous flood field. However, an ideally homogeneous field is not easily to achieve, since the dose profile of a linear accelerator's beam is not perfectly homogeneous (nor is it perfectly symmetrical). The invention thus makes use of the fact that a real beam profile (be it from a linear accelerator or an X-ray beam) is not expected to have high frequency components. Moreover, at the field borders of MV photon beams, it is also likely to detect a more homogeneous dose distribution along lines which are rather parallel to the beam's limits than perpendicular to them. Taking this into account, the clean gain image, as separated with steps described in the first part of the invention above, can be low pass filtered and considered to be a first estimation of the flood field's dose distribution over the panel's sensitive area. Iteratively, this estimation of a beam profile can be used to influence a consecutive separation result, by dividing the native signal, reduced by the clean offset, by the estimated dose distribution and adding the clean offset at the end before entering the next iteration with applying the separation as described in steps in the first part of the invention.

Accordingly, the second aspect of the invention provides a method of gain separation of an imaging device, comprising the iterative steps of: (a) providing an $n^{th}$ order estimation of the dose profile image of the beam irradiated onto the imaging device (which can be uniform in a $0^{th}$ order first guess); (b) subtracting from the uncorrected flood field image the clean offset image; (c) dividing the result of the subtraction by the estimated dose profile image of the beam to derive a pixel sensitivity image; (d) multiplying the result of the division with the doserate of the beam at a central pixel of the imaging device to renormalize; (e) adding the corrected offset image to obtain a gain image with the influence of an inhomogeneous flood field eliminated; (f) separating this flat image according to the steps in the first part of the invention to eliminate line artifacts; (g) multiply with the estimated dose profile image of $n^{th}$ order; and (h) low pass filter this image to derive a $(n+1)^{th}$ order estimation of the dose profile image of the beam irradiated onto the imaging device. Steps (b) to (h) can be repeated until the estimation of the dose profile is converging to a stable value, typically less then 5 iterations are needed. No further iteration is required to calculate the pixel sensitivity image of a panel if a dose profile is provided from separate image analysis or independent measurements in advance.

It has been found by the inventor that clean offset images and clean gain images as processed in step (f) above show the same distribution of high frequency texture over a large range of doserates: If window and level was adjusted properly, clean offset and clean gain images appear to be almost identical in aspect. Therefore, it turned out to be possible to find a correlation in between a clean offset and a specific clean gain image acquired at a certain doserate and in between native offset and native gain images as well, and thus enable to derive gain images for several doserates from a given offset image without additional measurements. This is especially of interest for further image corrections and improvement of long term stability as described below, since both offset and gain images are changing with time and temperature, and time consuming flood field calibrations are not possible to achieve during clinical operations.

Therefore, a further aspect of the present invention relates to dynamic offset correction using a background image. The background image acquired with an imaging device such as an amorphous silicon panel describes the dark field, i.e. the panel signal without any radiation. The background image is significantly varying with temperature and age of a panel. Therefore, according to this aspect of the invention a method is provided to acquire a dark field image immediately before the radiation is turned on and correct the clinical image for changes in the offset. Currently available medical flat panel software does already consider dynamic background measurements. As a new aspect according to the invention, the acquired offset image is separated from ghost contributions and moreover used to modify the doserate vs. pixel signal curve, i.e. the gain images of the panel. The modified curve is then used for image correction. This dynamic offset measurement is advantageous in that it can be done automatically between treating patients during the day, and no additional calibration work of engineers or physicists has to be done, which is highly important in clinical environments.

Accordingly, the present invention provides a method of image correction comprising the steps of (a) acquiring a background image from a non-irradiated imaging device immediately before the imaging device is exposed to radiation to be converted into a target image; (b) separating the ghost content from previously irradiated beams from this image; (c) modifying the existing doserate response relationship of the image device based on the acquired background image; and (d) correcting the target image using the modified doserate response relationship.

The step (c) of modifying the doserate response relationship of the image device based on the acquired background image preferably encompasses shifting the offset value for doserate 0 of the existing, i.e. previously determined and stored, doserate response relationship curve to the actual value of the acquired background image. The doserate response for higher doserates is affected to a lower degree; therefore the amount of the shift is decreasing with increasing doserate. Such a behaviour could, for example, mathematically be expressed by an exponentially decreasing function with a decay factor, which is typically comparatively small to the median offset value of a subpanel's row. The inventor found, that there is a relationship between the decay factor and the median offset value of the subpanel's row, phenomenologically.

Other phenomenological descriptions of this behaviour—modification of the doserate response curve based upon a changed background image can also be found and applied.

The method of this aspect is preferably performed when the time elapsed since the last image was captured, i.e. the panel was irradiated, exceeds a preset threshold to ensure that any lag (ghost) information of previously irradiated beams has vanished. The threshold is for example 5 minutes. Preferably, a second time threshold is taken into account, i.e. the time lapsed since the last valid background measurement was performed. Such threshold is larger than the first threshold and for example 7 minutes, and guarantees that an imaging device will not just be busy with capturing background images.

Preferably, the acquired background image should not contain any content (lag) of previously irradiated beams if the image is used to derive or modify temperature dependent gain images.

According to a preferred embodiment, if the time interval since the most recent background image was taken exceeds the first threshold at the time right before the panel is to be irradiated again, a ghostly image will be captured and compared to the latest available ghost-free offset image. The difference between these two pictures is calculated in order to extract the ghost content from the real background.

If the latest available measurement of ghost-free offset images exceeds a third threshold, so that there might have been relevant temperature changes between the time of last valid offset measurement and recent ghostly offset measurement, a simple subtraction of images would yield in a ghost image with temperature dependant COB artifacts. Therefore, as a more sophisticated approach, a further aspect of the invention relates to deriving a ghost-free background image from a ghostly background image captured immediately before a panel is to be irradiated.

For this aspect of the invention it is assumed (and has to be ensured) that not the entire area of the panel is irradiated with beams, e.g. while taking a MV portal image. Areas, that have not been irradiated do not show any image lag (ghost) and such pixel values are therefore identical to those in the actual ghost-free offset image. By analyzing the difference of the recently captured ghostly offset image with the last valid ghost-free offset image in non-irradiated regions of the panel, only temperature dependent changes in COB artifacts can be found. By calculating the median of the rows in such areas and deriving their difference in both images, temperature dependant changes of subpanel row's can be applied to the latest available ghost-free offset image in order to receive an estimation of the actual ghost-free offset image and thereby overcome the need of measuring it directly. In a clinical environment, panels are irradiated at high frequencies with rather short times in between two beams.

A further aspect of the invention relates to the determination and correction of the doserate response relationship for low doserates. It has been found by the inventor that the doserate response is quasi linear above a certain doserate only but that it is substantially non-linear below this doserate. It was further found that especially at low doserates the aging of the panel and the actual panel temperature during use substantially effects the doserate response. In the context of the present invention, the term "low doserate" means a doserate below the doserate at which the non-linear doserate response passes over to the quasi-linear response, and the term "high doserate" means a doserate above the doserate at which the non-linear doserate response passes over to the quasi-linear response.

Conventionally, absorbers were used to reduce the doserate at the detector or—in a scientific environment—the detector was just moved away from the source to a limited extent. However, all these conventional methods require an additional, detector independent measurement that records the delivered doserate time dependently and correlates frames and pixel values to the actual measured dose in a specific pixel at a certain time within measurement—which is not so easy to do. Ionization chambers that were used to record the doserate give the doserate in a point (a small volume) only. Furthermore, metallic absorbers change the beam quality and thereby influence the response to some extent in another way. Water-equivalent absorbers have to be very thick and heavy to reduce the doserate to below 5%, which is impractical.

Thus, according to the invention, in a preferred embodiment, low doserates and variations in doserate were accomplished by changing the pulse repetition frequency of the radiation source, for example the linear accelerator instead of bringing different absorbers into the field. The actual doserate on the detector is measured directly and accurately by the monitor chambers built in the linear accelerator's head. The actual measured doserate is exported and read out so that each single captured frame from the panel can be correlated.

Accordingly, the invention provides a method of image correction comprising the steps of (a) emitting radiation from a radiation source at a desired low doserate; (b) detecting the actual doserate; (c) detecting the signal response at an imaging device; and (d) calibrating the doserate response relationship using the detected actual doserate and the detected signal response.

In normal use of the radiation therapy system, the radiated doserate is substantially higher than the doserate emitted in step (a) because radiation is absorbed by the patient so that a substantially lower doserate actually reaches the imaging device. Thus, in step (a) radiation is emitted at a doserate that during use of the radiation therapy system typically exposes the imaging device. In other words, for calibration and correction purposes the invention suggests to intentionally emit radiation at low doserates that would be too low for taking images of a patient but corresponds to the doserate reaching the imaging device when taking images of a patient.

In step (b), the actual doserate is preferably detected directly at the radiation source, e.g. by means of the monitor chamber in the linac's head.

Since the doserate of a linear accelerator can be varied in discrete steps only, it is possible to add additional measurement points to the doserate response curve by inserting water equivalent absorbers (for example PMMA sheets), which absolute absorption rate was measured with an ionization chamber in the central axis at detector distance. Their relative absorption rate was measured in two dimensions by the primarily corrected panel itself.

Starting out from the idea of direct measurement of the doserate at the linear accelerator, the invention further provides for a multi level doserate calibration.

For multi level doserate calibration, first, an offset image is acquired and stored, giving the first point of the non-linear correction curve. It is preferred that this measurement is only be performed when the temperature of the panel is stable and no beam was irradiated onto the panel in the last few minutes, to ensure that any ghosting has vanished and will not be recorded in the offset image.

Next, at the lowest possible pulse repetition frequency (corresponding to for example 6 MU/min), a flood field is irradiated (preferably without any absorbers) directly to the centred panel. During beam start up, no frames are captured: Background frames, frames with non-symmetric dose distributions or such with lower signal shall not be integrated into the frame buffer, because this would negatively influence the accuracy of the measurement. When the actually reported doserate exceeds a predefined threshold value (e.g. 50% of the prescribed doserate), a timer starts. After a predefined time (e.g. 10 s), during which the signal further increases at constant doserate due to intrabeam ghosting effects, when the signal to doserate ratio is stable enough, a predefined number of frames (e.g. 40) is captured and added to an integration buffer. For each frame, the actual doserate is recorded. The average pixel response to the averaged doserate during the integration time can then directly be stored as a 2D image and represents the second point on the non-linear correction curve. This procedure is repeated with increasing doserates (for example, 12, 25, 50, 100, 200, 400, 600 MU/min) providing additional points on the non-linear correction curve.

Accordingly, the invention provides a method of doserate calibration comprising the steps of (a) acquiring an offset image of the imaging device, providing a first measurement point of the correction curve; (b) starting irradiating the imaging device with a radiation source; (c) detecting the doserate emitted by the radiation source; (d) initiating a timer as soon as the detected doserate exceeds a predefined threshold value; (e) acquiring a predefined numbers of image frames after a predetermined time interval; (f) recording, for each frame, the actual detected doserate; (g) determining the average pixel response of the imaging device to the averaged doserate of the acquired image frames as further measurement point of the correction curve; (h) repeating steps (a) through (g) for increasing predefined doserates.

The predefined threshold value is preferably 50% of the prescribed doserate. Furthermore, the predefined time interval is preferably 5 to 15 s. The predefined number of image frames is preferably 20 to 40.

The invention also encompasses combinations of all or at least some of the calibration and correction methods described above. These methods were explained separated from each other for ease of explanation which should not be construed as limiting the invention to the individual methods.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts, and wherein:

FIG. 20 shows another example with respect to automatic registration of images allowing an immediate overlay of beam's aperture and internal patient structures.

DETAILED DESCRIPTION

Figure 1:
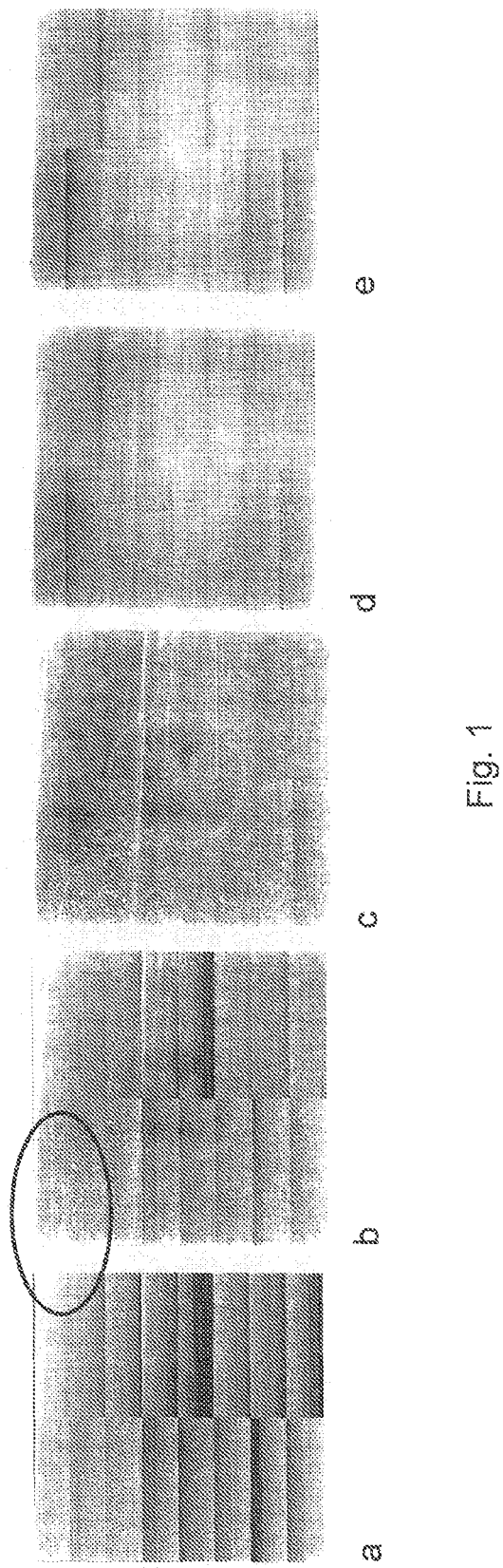
FIG. 1 shows uncorrected (native) images of an old panel at different doserates.

Background images of older panels show disturbing horizontal lines parallel to the long sides of the panel. This is shown, as an example, in FIG. 1. FIG. 1 shows uncorrected images of an old panel at different doserates. As can be seen, the dark offset stripes are rapidly disappearing with increasing doserate which is in FIG. 1a 7 MU/min, FIG. 1b 25 MU/min, FIG. 1c 50 MU/min, FIG. 1d 100 MU/min and FIG. 1e 400 MU/min. These high intensity (dark) rows in the offset image vanish rapidly on irradiation with very low doserates (FIGS. 1a-c), and on increasing doserates the stripes turn continuously lighter, indicating that the relative pixel sensitivity for the pixels in such poor rows is significantly decreasing at very low doserates to values comparable to better pixels in other rows.

The remaining stripes in the images acquired at higher doserates—deviations in the response of different rows in different sub panels—are not necessarily located in the same rows as seen in the offset image, and their relative difference to neighborhood rows is of lower magnitude.

If irradiated with a perfectly homogeneous field at a higher doserate, statistically, all pixels in a specific sub panel row show a standard deviation to the low pass filtered pixel values along that row, which is correlating to the median value of all pixels in the row at that doserate: The higher the median, the lower the deviations in the row, but even on the poorest rows, there is still some information. The correlation is stronger if some pixels, e.g. the non-uniformly distributed white speckles (highlighted in FIG. 1b by the black ellipse), were excluded before deriving the standard deviation from the median. A further increase of correlation can be achieved by separating the pixels located on the left side of the panel from those on the right side.

That means that the pixel sensitivity for a single pixel in a row can be described to have two components: one that stems from the row (sub panel readout system) and another component that is specific for the pixel itself (properties of absorbing and scintillating layers and of the photodiode at the pixel's position). The latter component varies from pixel to pixel in higher frequencies, direction independently. The first component can be described by means of a low frequency offset value per row (e.g. the median of the row) and an information amplification factor, which can be estimated from the statistical analysis, e.g. by calculating the ratio of information along good rows with lower median values to the information along the row concerned or by fitting a spline in the collected data and calculating the inverse.

Figure 2:
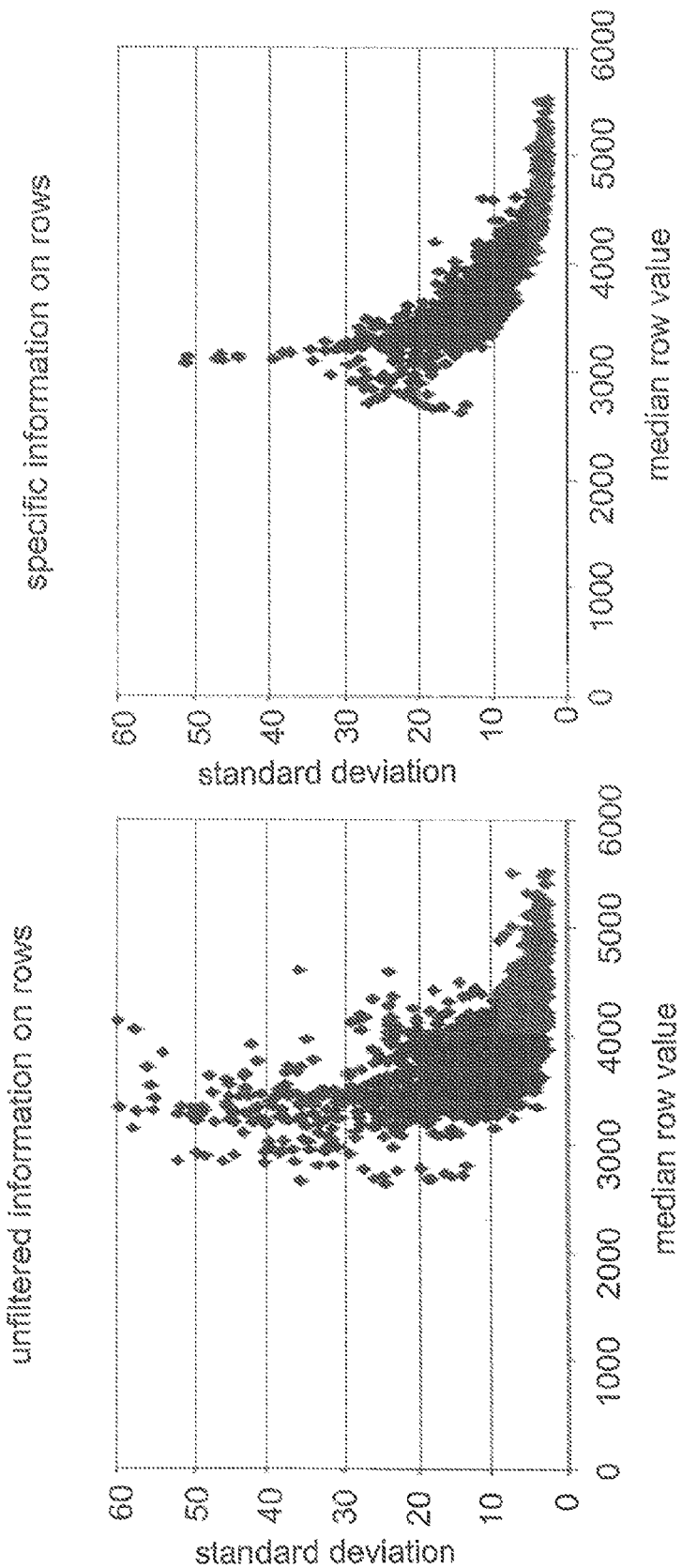
FIG. 2 shows signal amplitude as a function of median of pixel values in a panel row.

FIG. 2 shows signal amplitude (standard deviation) of 2048 subpanel rows as a function of median of pixel values in a subpanel row in an offset image of an aged detector. The left diagram shows unfiltered information, whereas the right diagram shows standard deviation along the row derived from those pixels, which deviations to the median of the row were in between an interval from 60% to 90% of the range between minimum and maximum on the row to exclude non equally distributed white speckles (0% to 50%) from the statistical analysis.

The fact that there is still information of higher frequencies on poorest subpanel rows and that a lower boundary above zero seemed to be reached for all subpanel rows with median offset values higher than 4800, gives reason to assume that aSi:H flat panel detectors will never completely die and corrections can be developed and applied to amplify the rest of information accordingly.

In the following, the separation of offset (or flat gain) images will be described in more detail.

It has been found by the inventor that the row specific artifacts in a native offset image stemming from the readout system can be separated from an underlying texture, which can be physically associated to properties of the absorbing and scintillating layers as well as of the photodiodes and structures beyond (backscatter). While the first part (artifact lines) is representative for the condition of the readout system, the second part can is describing the specific panel itself. Therefore, aging of the detector mostly changes the first part, while the second is merely affected. It can be assumed, that the second part is identical with the native offset image acquired from the new panel, provided that the readout system was working ideally at that point in time and the separation was done properly.

According to the invention, the separation can be done in different ways:

Under the assumption that the minimum value of all medians of all sub panel rows of the panel is the corresponding value for a new panel, the difference between each row's median and a lower sub panel row's median (near the minimum median row of the entire panel) can be said to be the disturbing part of the aged panel's offset image, whereas the remaining pixel value is the corresponding value of that pixel in the original, new panel.

An even more accurate separation approach makes use of the identified effect of weaker information of higher frequencies on the poorer rows with higher medians. The disturbing part can then be extracted by low pass filtering each subpanel's row and shifting this function towards a median value of the whole panel. The difference to the native image is then a constant value plus the high frequency part and can be considered to represent the offset image of the perfectly new panel.

Other approaches may make use of a fast Fourier transformation to do the separation in the frequency domain directly before performing a back-transformation of the result.

Figure 3:
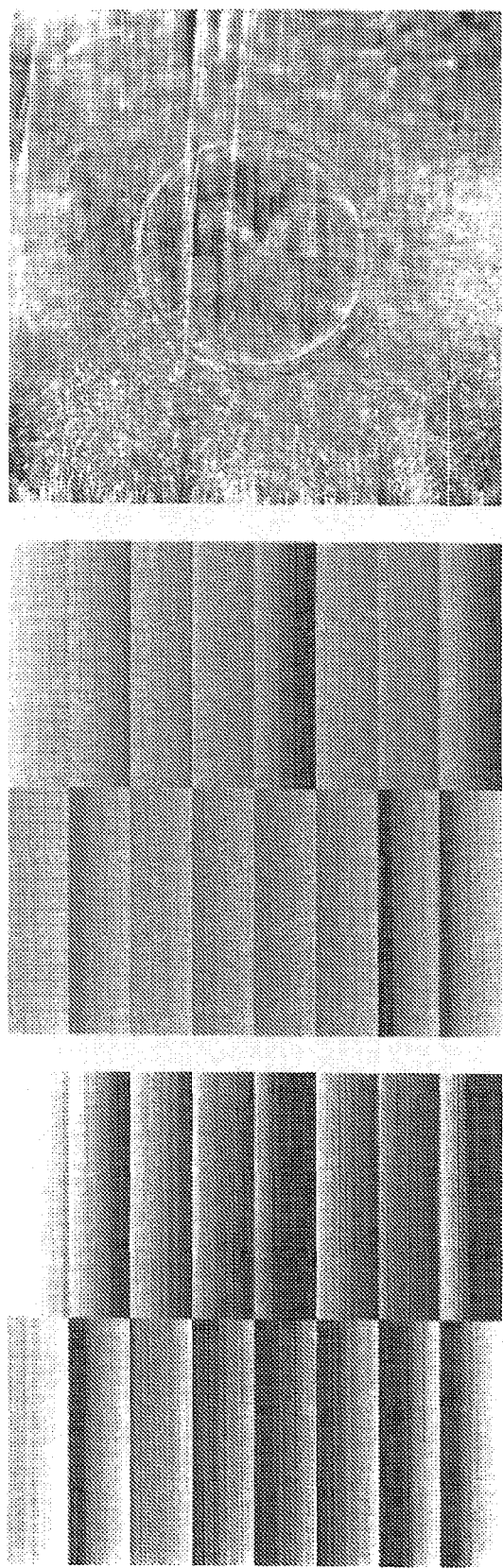
FIG. 3 shows the separation of a native offset image in row specific components and corrected (clean) offset image.
Figure 4D:
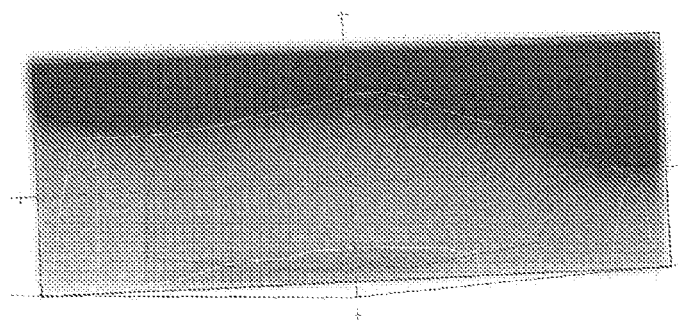
FIG. 4 is an example to show that the present invention provides improvements at different doserates.
Figure 4C:
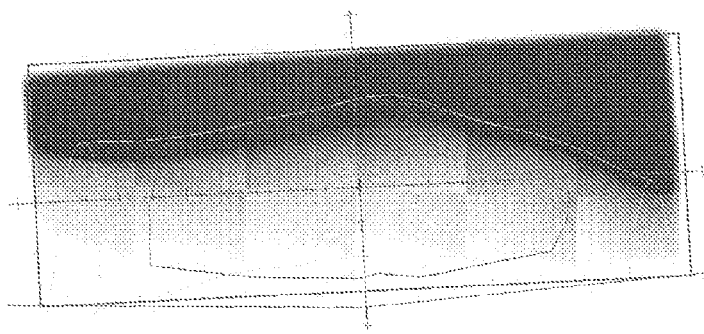
Figure 4B:
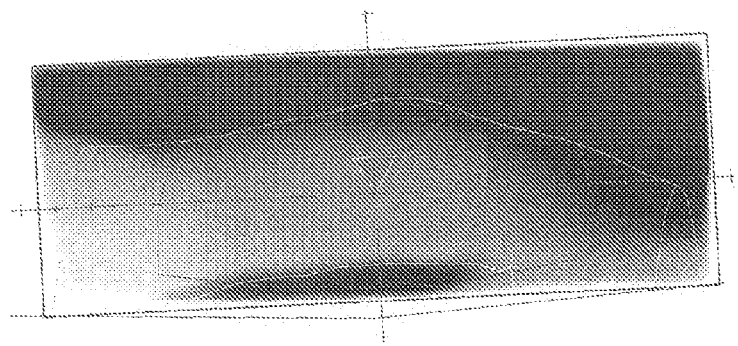
Figure 4A:
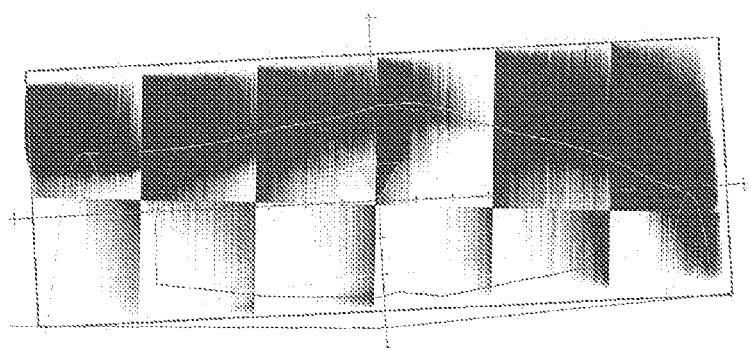

FIG. 3 shows an uncorrected offset image of an old panel with a maximum intensity value of 5000 in poor lines (FIG. 3a), separated in row specific components (maximum intensity value of 2500) (FIG. 3b), and the corrected (clean) offset image (maximum intensity value of 3000) (FIG. 3c). The difference between each rows median and the minimum sub panel row median of the panel is calculated (in the drawing FIG. 3a–FIG. 3b=FIG. 3c). The mean value in the corrected offset image is approximately 3000, as for new panels. Image (c) clearly indicates that there is still useful information even on the very poor rows of an aged flat panel, although covered physically by incorrect bias voltages of the electronic components of the readout system.

The improvement of the image by applying "ideal" offset correction is shown in FIG. 4. Simply taking the clean offset value instead of the native offset value produces clinical images of much better quality, if just one gain image is provided (linear gain offset correction). FIG. 4 is an example to show that the present invention provides improvements at different doserates. FIG. 4 shows irradiation of a female breast with 6 MV photons. In FIGS. 4a and 4b, a wedged beam was used, i.e. the beam had to pass a tungsten wedge which reduces the doserate as it absorbs radiation. In FIG. 4a conventional gain-offset correction was applied. FIG. 4b shows the same picture with offset separation correction applied only (=linear correction, just one gain image). In contrast thereto, FIGS. 4c and 4d show the same female breast, however irradiated without a wedged beam, i.e. higher doserates. In FIG. 4c, again, conventional gain-offset correction was applied, whereas in FIG. 4d, correction according to the invention was applied (offset separation). It can be seen that the method works at lower doserates.

The separation according to the invention can also be applied on gain images, provided, however, that the gain image was acquired by irradiation with a perfectly homogeneous flood field. An inhomogeneous calibration field would introduce an additional low frequency response and thereby cover row specific properties. Typically, an ideally homogeneous field cannot be easily achieved, since the dose profile of a linear accelerator's beam is not perfectly homogeneous (nor is it perfectly symmetrical). The same problem occurs on kV flat panels irradiated with X-ray sources. However, both flatness and symmetry of the irradiation field, are specified to be within defined tolerance levels of a few percent at certain field sizes and beam energies of linear accelerators. Additionally, a real beam profile (linac or X-ray) is not expected to have high frequency components—a typical beam's fluence profile will always be smooth and some rotational symmetry in the centre of a large field can be expected. At the field borders of MV photon beams, it is also likely to detect a more homogeneous dose distribution along lines which are rather parallel to the beam's limits than perpendicular to them. Taking this into account, the low pass filtered texture extraction of a native gain image can be used to derive a first estimation of the flood field's dose distribution over the panel's sensitive area. Iteratively, this estimation of a beam profile can be used to influence a consecutive separation result, by dividing the native signal, reduced by the clean offset, by the estimated dose distribution and adding the clean offset at the end before low pass filtering the rows. Alternative methods to separate the influence of an inhomogeneous flood field iteratively can be also used and some of these approaches are described below.

However, this fairly simple method according to the invention yields comparatively accurate and fast results for beam profiles, and it was surprisingly found that it works on totally uncalibrated panels; the separation method according to the invention does not require a calibration before. All alternative methods, including independent water phantom measurements, film dosimetry or Monte Carlo simulations either lack the benefit of enabling to measure the actual two dimensional profile simultaneously with the pixel response and/or show problems due to the fact that dose profiles measured in matter are always strongly depth dependant, and there are difficulties to determine a proper measurement depth compared to the effective measurement depth of the photodiodes/scintillating layer in the panel, and selection of proper ionization chambers/build up is also sophisticated. Furthermore, linac beam profiles are varying to some extent from day to day and also with doserate. Different panels may have different absorption layers of different depth, the effective measuring depth differs from diode to diode within one panel, at least increasing on an average with distance to the beam's central axis due to ray divergency.

Alternatively, an additional flattening filter (compensator plate) could be used per beam energy, manufactured of easily available material such as PMMA (plexiglass) and mounted on the shadow tray or positioned on the panel directly to modify the fluence. However, for not too bad panels, it turned out so far that the correction according to the invention is sufficient to eliminate beam inhomogeneities for further considerations. As a relevant side effect, by separating beam properties from panel properties, all further panel calibration procedures can be performed with just one beam energy, with the advantage of significantly reducing the required time.

Figure 5:
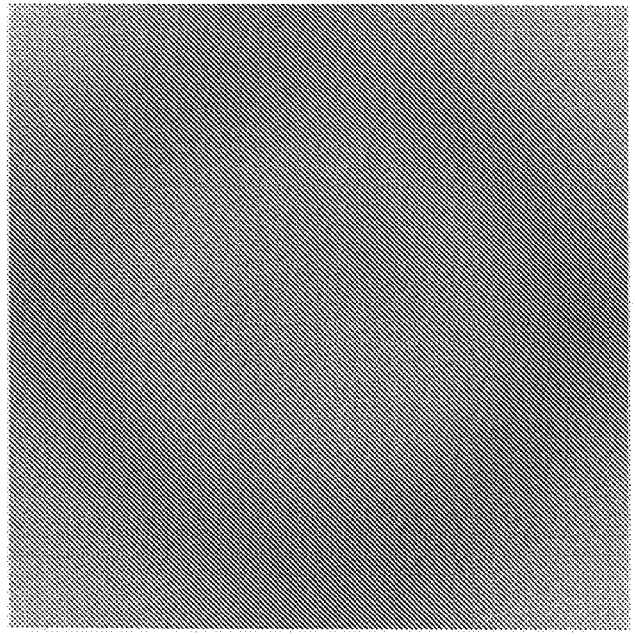
FIG. 5 visualizes dose distribution across the panel during flood field measurement.
Figure 5:
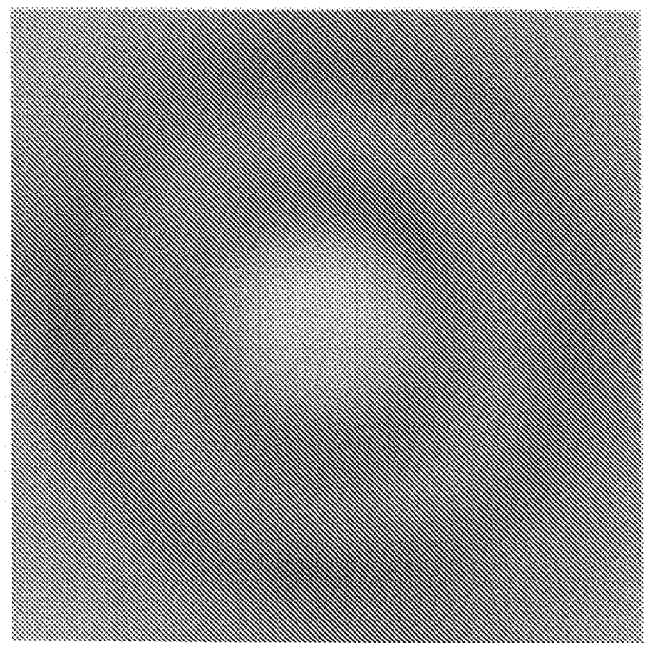

To give an example, FIG. 5 shows the extracted doserate in the effective depth of the scintillating layer after one iteration due to non uniform particle fluence during a flood field measurement at (a) 15 MV photons at 200 MU/min (left picture), and at (b) 6 MV photons at 200 MU/min from the same aged panel (2½ years full clinical use) (right picture). A margin of 64 pixels width around the panel was not included in the analysis to safely exclude the physical beam borders (MLC) in this case. The flatness was derived to be 1.5% for 6 MV and 2% for the 15 MV beam from this measurement.

Figure 6:
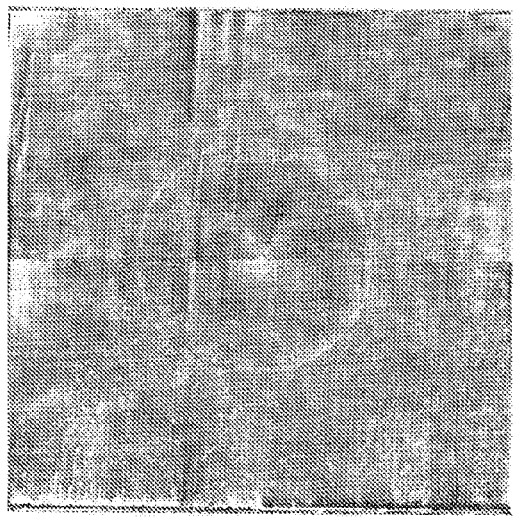
FIG. 6 relates to flood field measurement.
Figure 6:
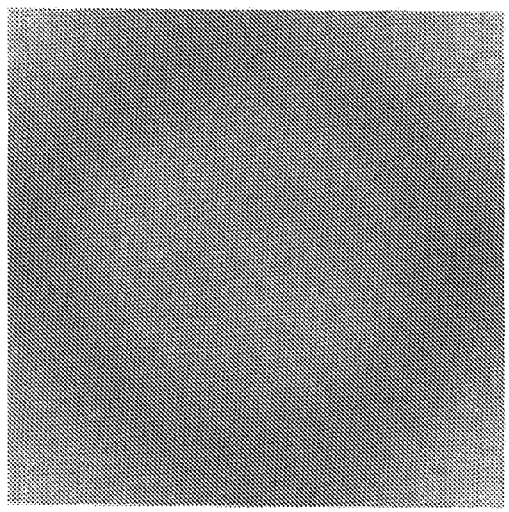
Figure 6:
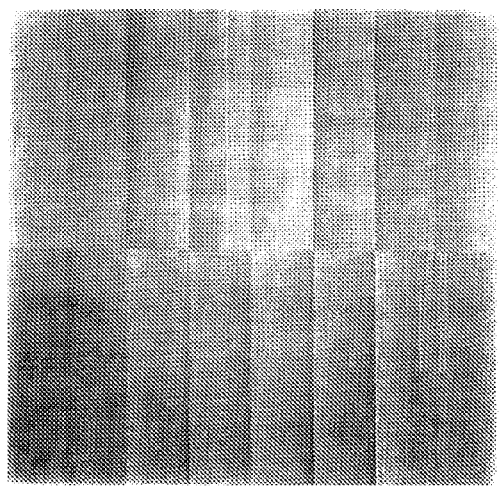

FIG. 6 shows the effect of iterative gain separation after doserate extraction: in a first step, the native response image (left picture) is separated according to the same rules as for separating the offset image; the resulting clean gain (without remarkable row differences) is then reduced by the clean offset image in a first approach and undergoes a low pass filtering with averaging regions according to the symmetry and flatness assumptions to be expected from independent measurements to enlarge the statistics wherever possible. The result (centre picture) is considered to be the first order estimation of the beam's dose profile, or more accurately, what the beam fluence had induced in the scintillating layer. By correcting the native flood field image with this doserate (subtract the clean offset in a first approach, divide by the beam's doserate image, multiply with the beam's doserate at a central pixel and finally add the clean offset to reach the same level it had before) a consecutive separation can be executed to derive clean gain images of any order. These images are considered to be identical to an ideally new panel's response on irradiation with a homogeneous beam at a given doserate.

The proposed iteration rapidly converges to stable doserates and clean gain images, if very poor subpanel rows are excluded from the statistical analysis of expected uniform regions within the beam.

Figure 16:
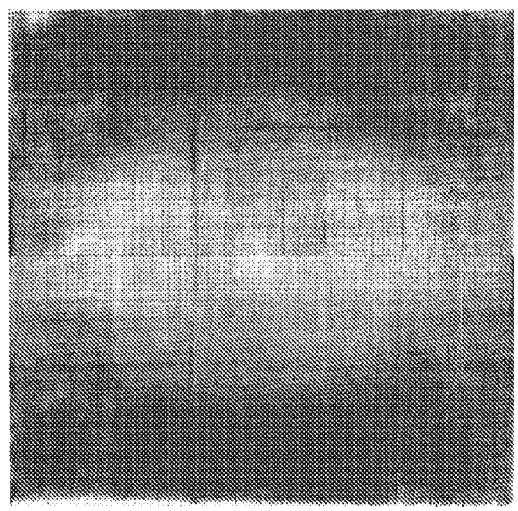
FIG. 16 shows the effect of dividing the signal image by the extracted texture of the offset image.
Figure 16:
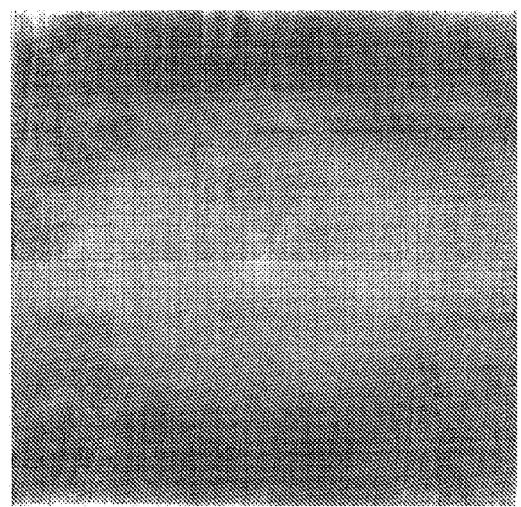
Figure 16:
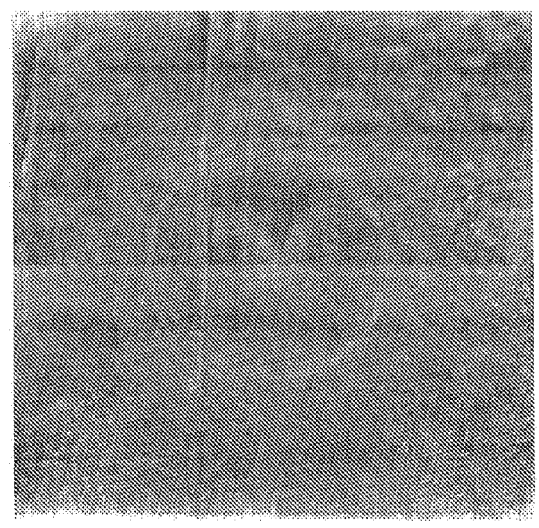

The effect of dividing the signal image by the extracted texture of the offset image is shown in FIG. 16. FIG. 16a shows an old panel's signal image while irradiated with a flood field at 400 MU/min; this image was processed by eliminating the vertical stripes and amplifying the signal amplitude per sub-panel row: the texture impression is the same as in the offset image. FIG. 16b shows clearly that subtraction of the texture of the offset image is not sufficient: while some parts are disappearing (the concentric rings) other parts can still be seen (speckles in the edges). FIG. 16c shows the result of texture elimination by division of the processed signal image by the processed offset image: speckles and rings disappear. Furthermore, the remaining image is approximately the dose distribution of the flood field in the detector plane, and corresponds well with water phantom measurements.

The above shows that the clean gain images and the clean offset image show similarities. At a first glance, if window and level are adjusted properly, their aspect could be considered to be almost identical in many details. Most of the white speckles, concentric rings and darker scratches in both clean offset and clean gain images appear to give the same overall impression. Only at highest doserates some differences become apparent, which might be attributed to inaccuracies of the separation methods to some extent.

However, a simple subtraction of the clean offset image from the clean gain images fails in the attempt to generate a flat image: The overall aspect of a derived difference image is still similar to the offset. To some degree, the clean offset image was found in the clean gain images multiplicatively. Dividing a clean gain by the clean offset produces almost flat images. This finding is consistent with the concept of readout of charge coupled devices (CCDs), where the offset image is acquired by means of constant bias voltages addressing rows. The read out current per row is then amplified and processed to derive the offset image. An additional constant charge current will be generated per row on irradiation with a flat flood field. The resulting image should not differ significantly from the offset as long as amplifiers work in a linear range. Interpreting the results so far, for absolute dosimetry purposes/quantitative imaging, it would eventually be better to operate the panel with frame read out times suitable to collect rather low read out currents: Although the images might be disturbed by row specific read out artifacts (which was shown can be eliminated), it is more likely that the amplifiers work in a linear range.

Figure 7:
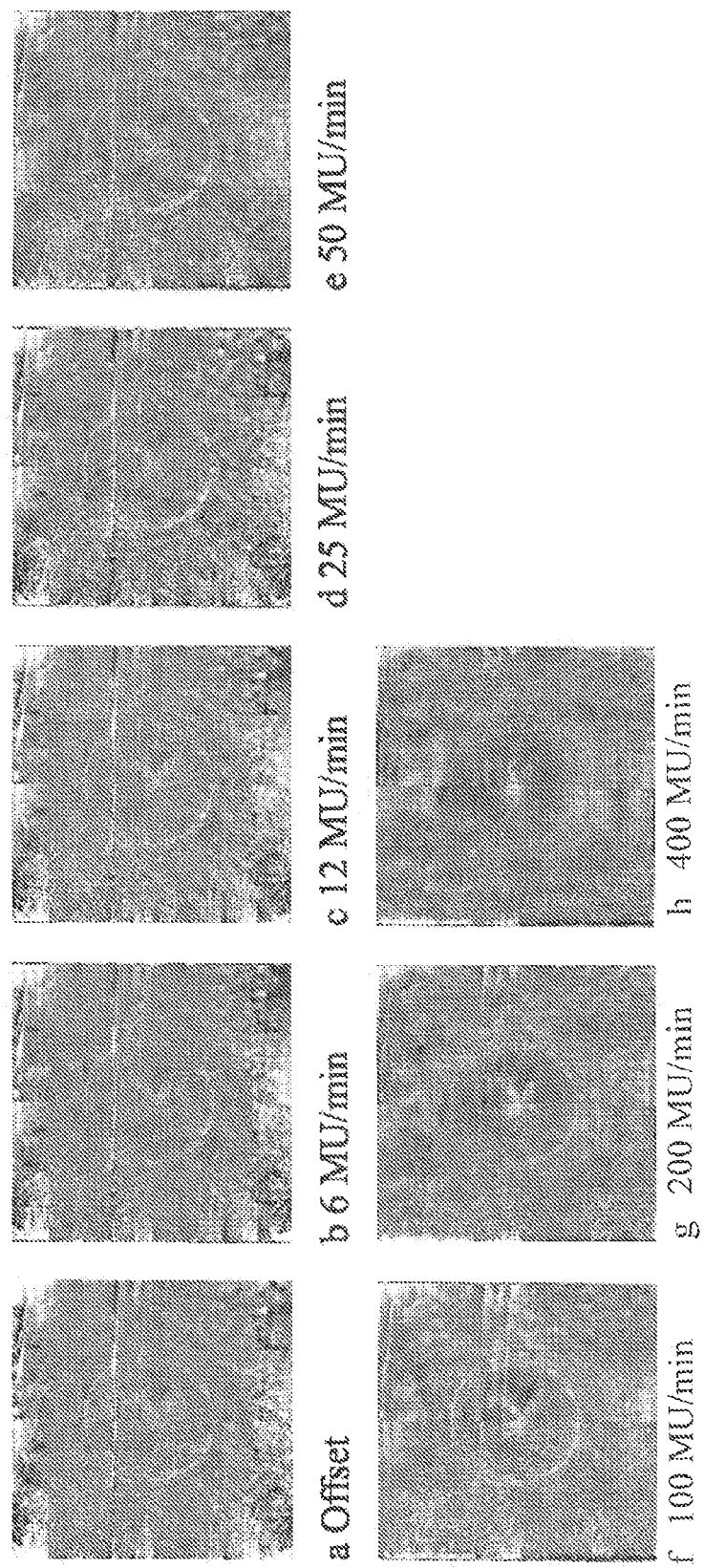
FIG. 7 shows various clean gain images for different doserates.

FIG. 7 shows clean gain images, derived from native images after subtraction of the row specific offset values, row specific amplification of texture information and division by the previously extracted doserate.

Therefore, according to the invention there is a doserate dependant correlation between gain and offset images. Such a quantitative correlation results in the possibility of generally deriving clean gain images from a supplied offset image. Such a correlation gives a requested dose response curve for an ideally new panel. This is eventually helpful when one is attempting to overcome age and temperature dependencies of panels, because background images can be acquired throughout the day very easily, while the conventional acquisition of gain images requires time consuming calibration procedures and flood field measurements.

The so found correlation between gain and offset can be used to modify the steps in the iteration described above with respect to gain separation. The "first approximation" method described there (subtraction of the offset image from the gain before dividing the difference with the estimated doserate) can be replaced with the here found correlation doserate specifically.

In the following, gain—offset correlation of native images is described.

A good row specific correlation can also be found between native offset and native gain, i.e. response to perfectly flat flood irradiation at a given doserate. For example, the correlation for one specific row can be derived by calculating a linear regression through data points, where each point is representing a pixel in the row having an offset and a gain value. For some of the rows in the panel, the linear regression fits the data points closely, indicating a high correlation coefficient. But for other rows, the correlation is not very strong. On exploring the reason, the inventor found that these rows showed a slight slope of intensity along the line. Some rows in the offset image appear to have lower signal values on the left than on the right end or vice versa, and so do rows in gain images. If the relative slope in the offset row differs from the one in the gain row, it is likely that the correlation will be weak, even if the information modulated on the row's slope is the same in both offset and gain. Therefore, before calculating the linear regression, the linear slope of each subpanel's row in gain and offset is derived and the data points are built to correlate from slope-corrected offset and gain values. Now, all rows show a much stronger correlation.

As an alternative and even more accurate approach, the slope does not have to be considered linearly. However, it is practical to describe just the linear slope and offset from the centerline of the panel as additional properties of the subpanel's row. $2_{nd}$ order or $3_{rd}$ order terms could also be derived and stored as properties of the subpanel's row.

Figure 8A:
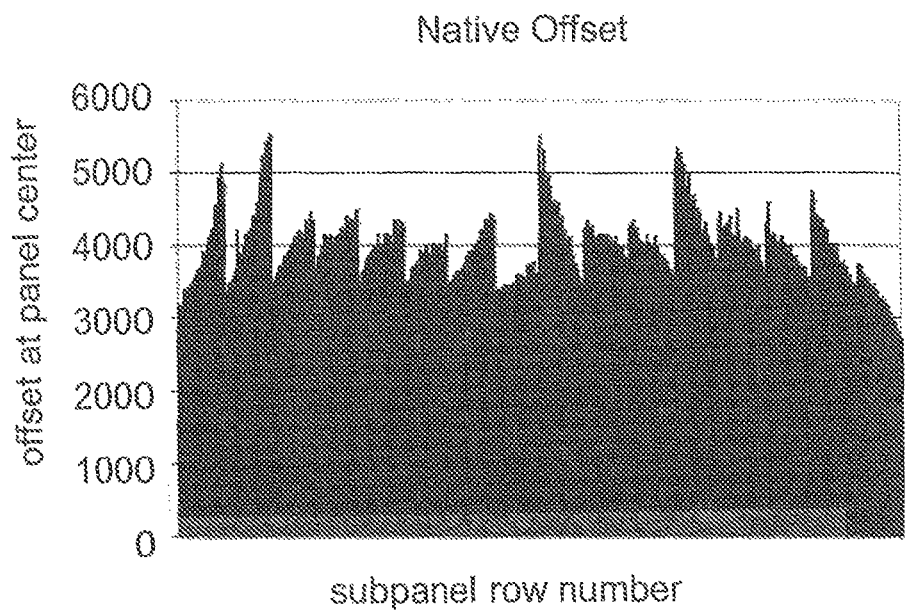
FIGS. 8a-d intercept and slope of pixel intensity along a subpanel's row.
Figure 8B:
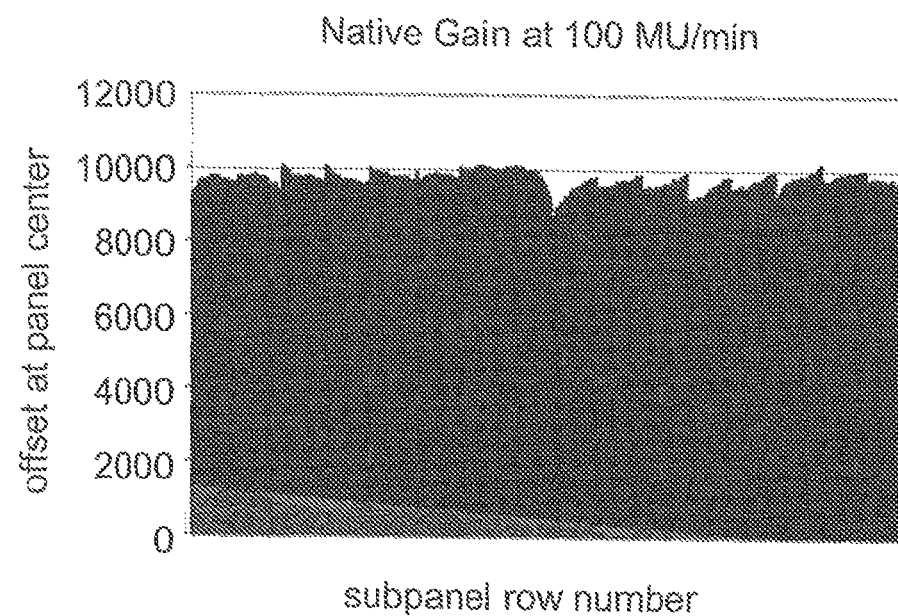
Figure 8C:
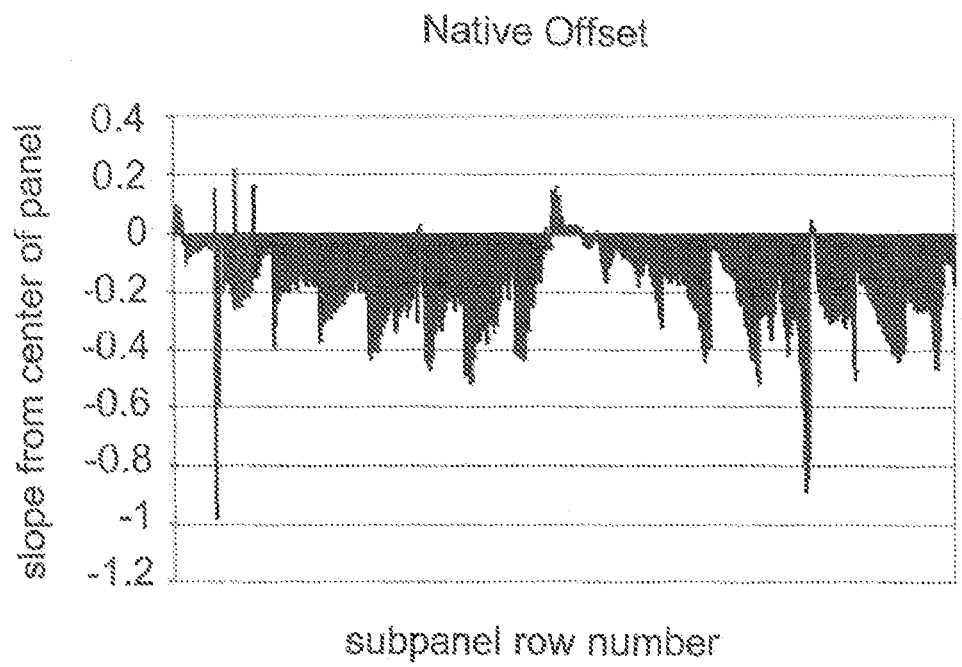
Figure 8D:
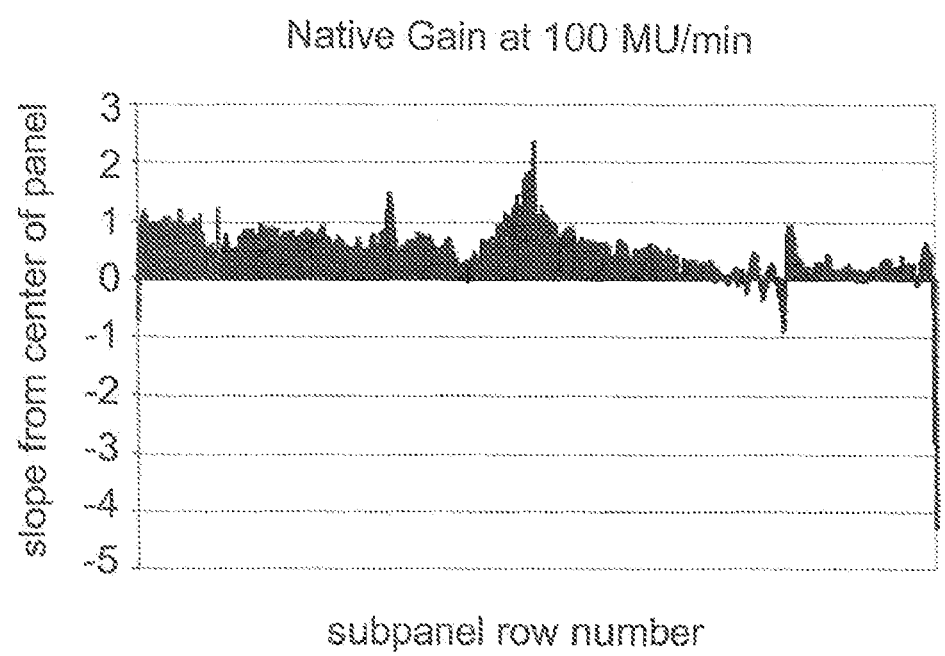

FIGS. 8a-d show intercept and slope of pixel intensity along a subpanel's row in offset (FIG. 8a, FIG. 8c) and gain image acquired at 100 MU/min (FIG. 8b, FIG. 8d). A slope of −1 indicates that the row shows decreasing intensity values towards the panel border, where the average pixel values in the center of the panel are 512 counts higher (one subpanel row comprises 512 pixels).

Figure 9:
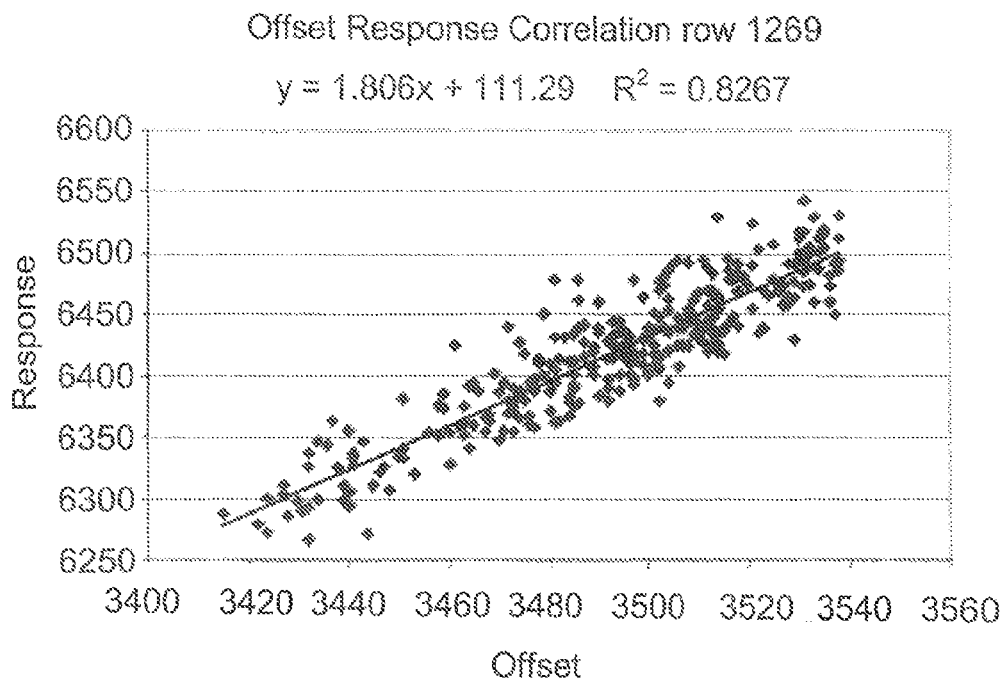
FIG. 9 shows correlation of slope corrected native offset and slope corrected native gain.
Figure 9:
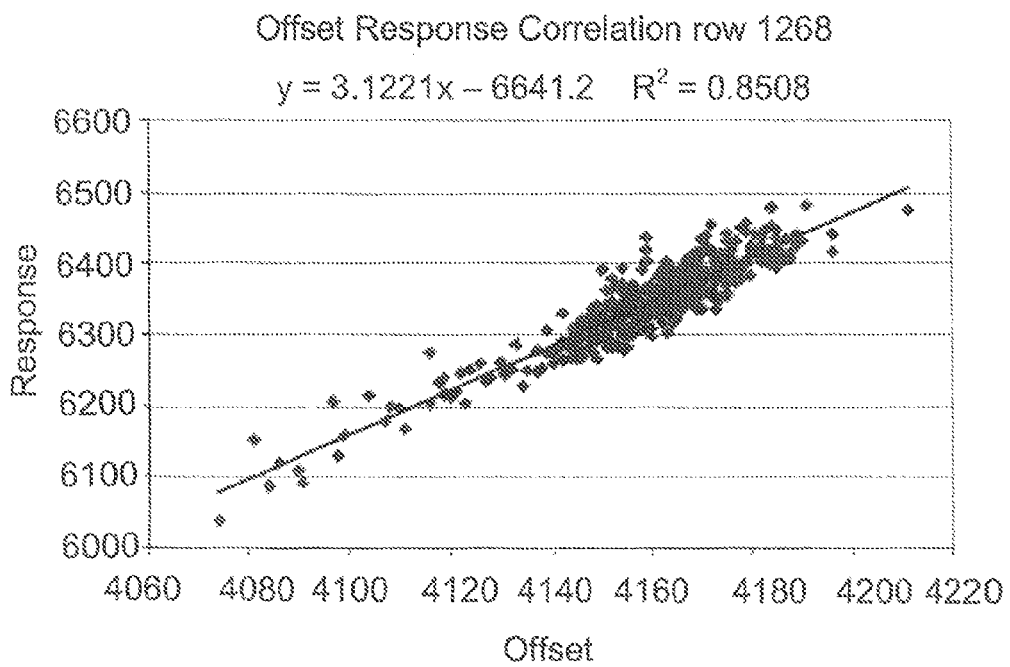

FIG. 9 shows the correlation of slope corrected native offset and slope corrected native gain for a better subpanel row (a, #1269, median offset 3490) and a worse subpanel row (b, #1268, median offset 4160). The correlation is good enough to be able to predict the gain image from a supplied offset image within an accuracy of ±50 counts out of 6400 (i.e. 0.8%) for that doserate. The remaining error can partly be explained by the limited accuracy of doserate extraction (failing on delivering a perfectly flat flood field) and by applying the simplified doserate correction (division after background subtraction).

In the following, the aspect of temperature correction is described in more detail.

The panel's temperature directly influences offset and gain signals. The higher the temperature, the higher both signals. Typically, the temperature of the panel is raising during clinical use over a few hours with the detector switched on until a constant level is reached. Irradiation of the panel with higher doses also influences offset and gain images beyond ghosting effects as if irradiation is changing the temperature, which could in principle be true at least for the components of the readout system due to electronic losses by powering amplifiers.

As a most relevant effect on aged panels, the destroyed amplifiers of the readout electronic introduce artifact lines which are unpredictably varying with temperature and time. This variations are of relevant magnitude, e.g. 500 counts of 5500 in a poor row's offset image within one day. Therefore, it is preferred and even desirable to measure the offset images throughout the day for correct compensation of clinical images as well as for dosimetric images, where parts of the images concerned are acquired with lower doserates at the panel due to absorption of energy in patients, phantoms or machine (e.g. wedge). However, the artifact lines in the gain images are temperature dependant as well. Their disturbing influence is decreasing with higher doserates as the artifacts are loosing dominance, but nevertheless, they are still present even after multilevel gain calibrations have been performed and are predominantly disturbing clinical images.

In more detail, temperature of the readout system does not just shift the average value of a subpanel's row, but it also changes its slope significantly. Another part of temperature related image changes is due to dependencies of the photo-diodes in the panel itself.

Both mechanisms (temperature effects on readout and temperature on panel) can easily be investigated simultaneously by measuring offset and gain at two different temperatures at least. The offset and gain separation can then be applied according to the rules described above, and row intercept values, row slope values and overall clean image median values can then be recorded in panel history files per doserate. A given gain image in provided calibration files can then be corrected for changes in temperature from analyzing the actual offset, comparing it with the offset at calibration temperature, conclude on changes in offset row intercept values, offset row slope values and overall offset median value, and look up a corresponding delta in gain row intercepts, gain row slopes and overall gain row median values in the provided history files by doing an interpolation in between the two values that were recorded from measurements at two different temperatures at least.

Figure 10:
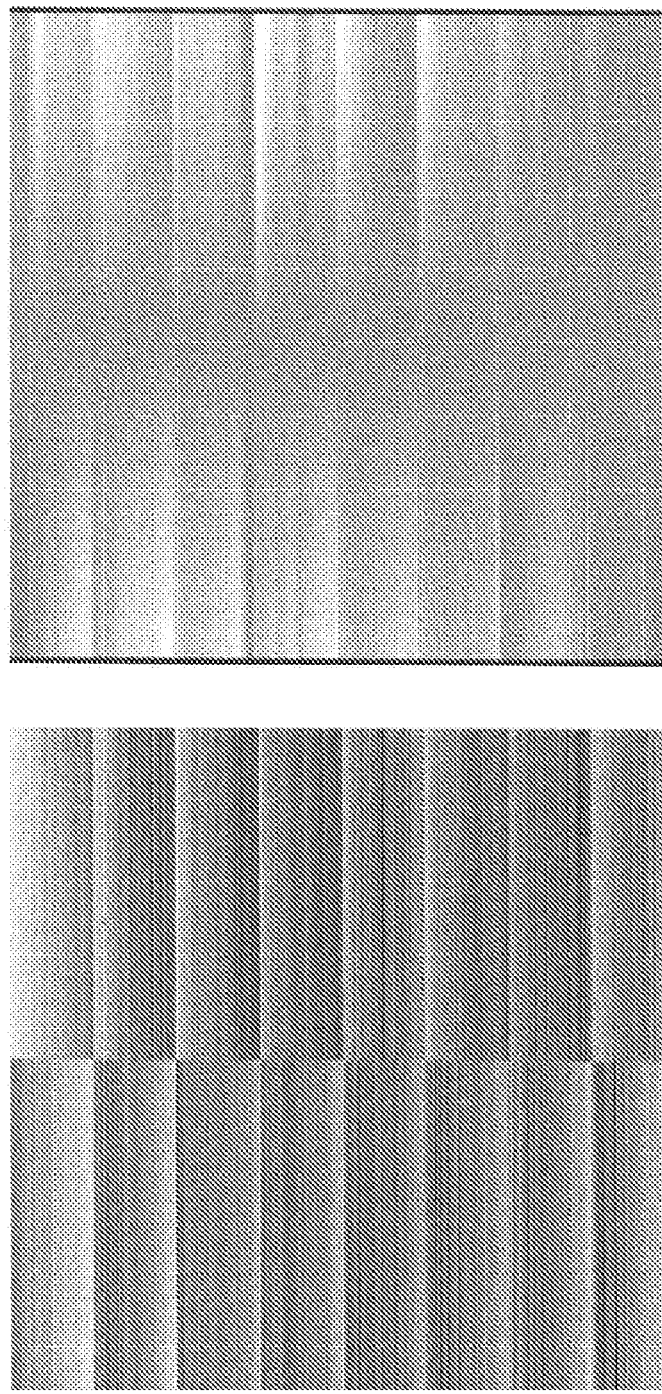
FIG. 10 shows the difference between two native offset images at different temperatures.

FIG. 10 shows the difference between two native offset images from the same day at different temperatures, wherein the right image is reduced by the intercept of each subpanel's row at the centre of the panel to make changes of each subpanel's slope visible.

Figure 11:
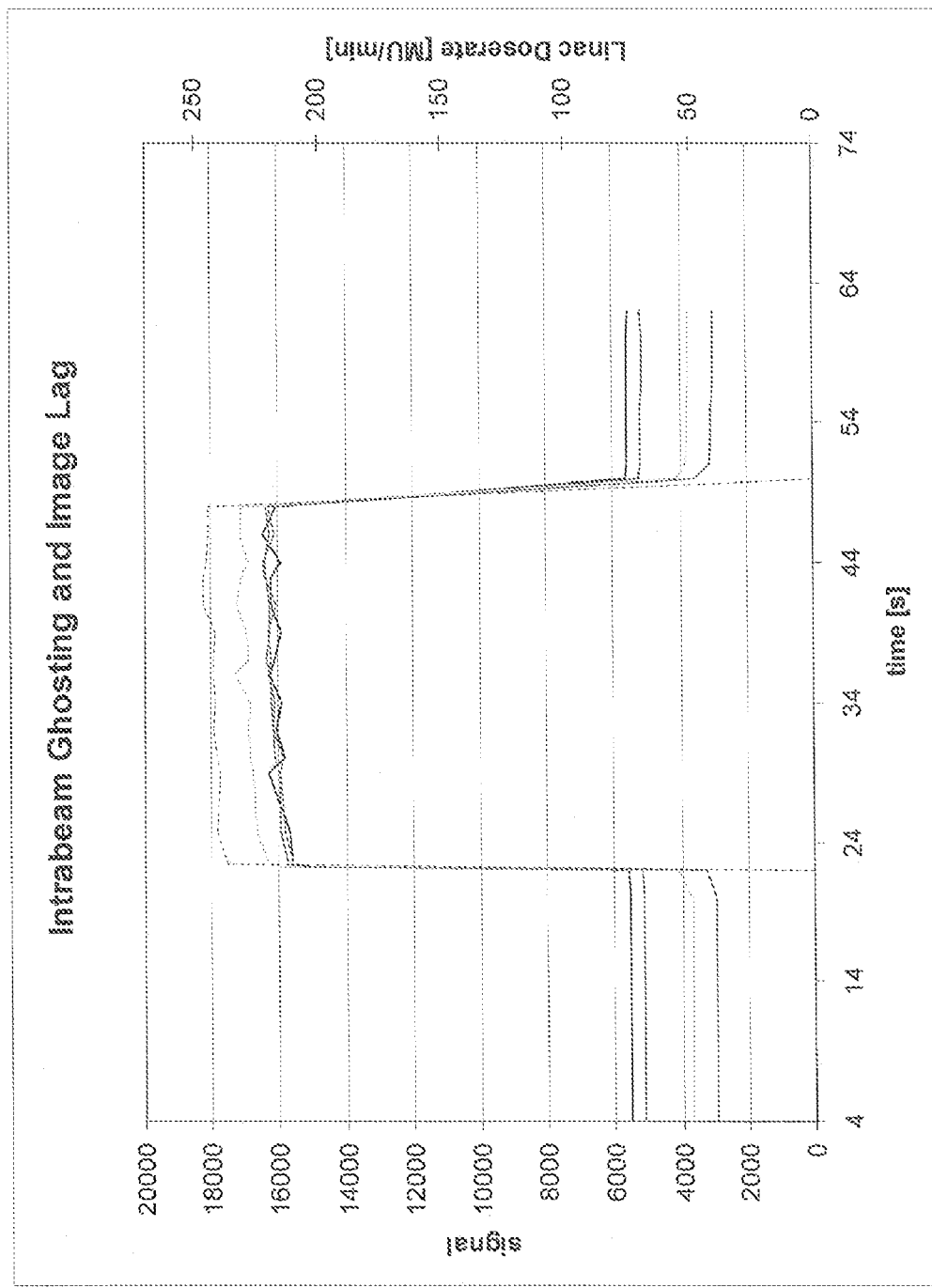
FIG. 11 visualizes that a pixel signal compared to linear accelerator doserate (dotted line) shows a time dependency for intrabeam ghosting and an image lag, after the beam is turned off.
Figure 12:
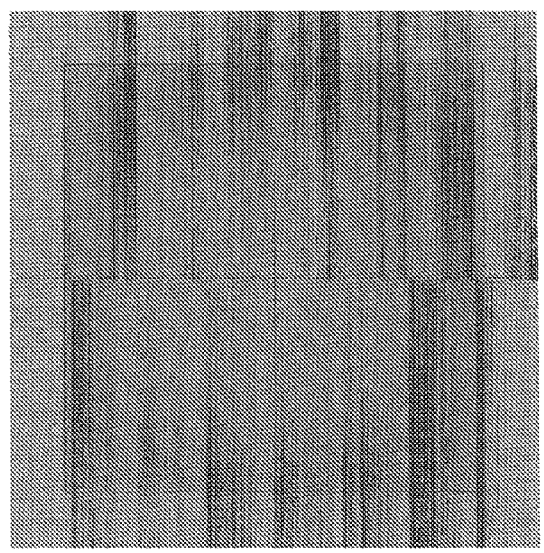
FIG. 12 shows image lag.
Figure 12:
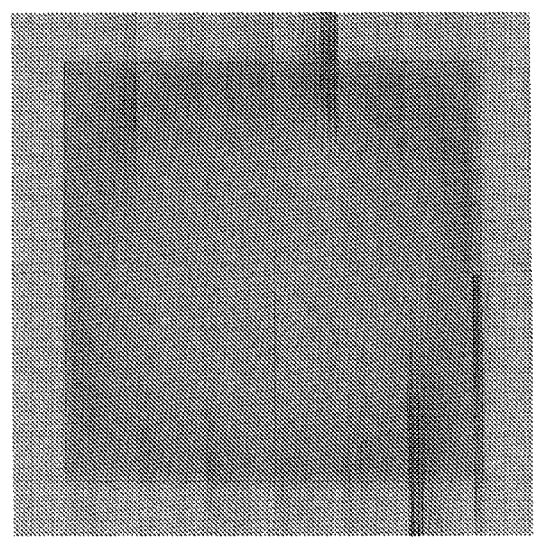
Figure 12:
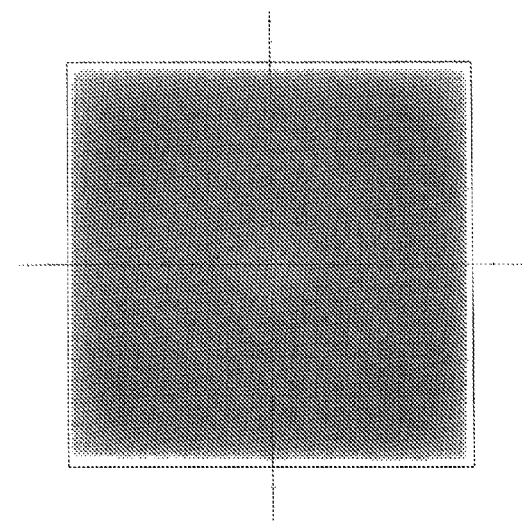

FIGS. 11 and 12 relate to ghosting and image lag effects. Mainly due to trapped charges and post-glowing of the scintillator, irradiations of areas with higher doses generate "ghost" images, that seem to be burned into the detector, as already explained above. Ghosting, intrabeam ghosting and image lag are roughly pixel independent: the poor rows in old panels show approximately same characteristic times to describe the decay than the good rows.

If the linear accelerator is ready to start or in a state between two segments in an IMRT field, a ghost image is captured from the panel, and the difference to the most recent background image (without ghost) is derived and kept in memory together with a timestamp. Since the decay of the ghosting effect in time is known (several components have been described in literature), given its start value, the ghost contribution to the pixel intensity of any subsequent frame can easily be calculated and subtracted from the native image. This procedure is not only relevant for IMRT step and shoot verification purposes, but also further improves image quality and reliability of single segment MV beams, when the total beam's monitor units are used to acquire integral portal images.

Intrabeam ghosting, which can be seen as an increasing signal at constant doserate per frame until an equilibrium has reached, can (and should be) compensated, if just a few frames are to be captured during low weighted beams and if applications related to absolute dosimetry are considered. Provided that a patient's anatomy is imaged, which is not moving significantly during image acquisition, so that the doserate at a specific pixel does only vary with the doserate measured in the linac's chamber, then, for a specific doserate, the effect of intrabeam ghosting can be calculated, mathematically using an exponential function $I_0[1-\exp(t/\tau)]$. FIG. 8 visualizes that a pixel signal compared to linac doserate (dotted line) shows a time dependency for intrabeam ghosting (build up of signal until a constant level is reached in ratio) and an image lag after the beam is turned off.

Image lag can be seen from FIG. 12. FIG. 12a shows the doserate of a 20×20 cm$^2$ field acquired with a poorly corrected, old panel (mean intensity 25000 counts). FIG. 12b shows the ghost image acquired 2 s after turn off of the beam (mean intensity 650 counts), and FIG. 12c 28 s afterwards (mean intensity is still 100 counts).

In the following, dynamic background is discussed in more detail.

During clinical operations, each time the linear accelerator of the radiation source is not immediately ready to start, not starting a segment and not irradiating, e.g. if the machine is in preparation mode, according to a preferred embodiment of the invention, offset images are acquired, separated and stored in memory and/or harddisk, when the time elapsed since the last portal image was captured (the panel was irradiated) exceeds a certain threshold (e.g. 5 min) and/or the time elapsed since the last valid background measurement was performed exceeds another threshold value (e.g. 7 to 10 min). This is accomplished with a separate offset acquisition thread within the application, and it was found that averaging one to five background frames is enough to provide a sufficient offset image, which is, as discussed, highly temperature dependant. If the actual offset image is used to derive or modify temperature dependant gain images, this offset image shall not hold any content (lag) of previously irradiated beams. Image lag/ghosting must be treated separately.

If the most recent background image is older than a certain threshold (e.g. 10 min), for instance due to the fact, that there is busy clinical operation with numerous beams and too short intervals in between to capture a ghost free background, then a ghostly image will be captured and compared to the latest available offset image. From the difference between the two, the subpanel row artifacts can be eliminated as described above, and the result can be considered to be equivalent with the pure ghost information. Subtracting the pure ghost from the most recent background image would yield in an estimated offset, that could be taken for further considerations as well.

An even more accurate approach is based on the fact, that most clinical images are of limited field size and positioned in the centre of the panel. Therefore, the right and left borders of the panel are likely to hold almost no ghostly components. Since the row specific properties are known for the panel from previous offset measurements and separations (median, intercept, slope), one can derive a totally ghost free background image from the ghostly image at actual temperature by adding artifacts (extracted from the ghost free margin) to the most recent clean offset image. Even temperature changes of row slopes can be taken into account by using the information in the panel history files as described above, since temperature related changes in row intercept or median of the pixel values in the ghost free margin are correlated to changes in the slope of the row.

A further preferred aspect of the invention relates to multilevel calibration.

The row specific effects as discussed above in detail have not yet been described in the prior art on such a detailed level so far. This is probably due to the fact, that most attempts to accurately determine the doserate response relationship were realized by measurements in doserate regions above a certain minimum value that was expected to be clinically relevant. Proposed procedures for multi level calibrations so far suggested to acquire gain images from flood fields at doserate levels above 50 MU/min. A technical obstacle on measuring response at very low doserates can certainly be identified in the limited accuracy of doserate production with a linear accelerator, especially at low pulse repetition frequencies (PRFs): Far from an optimal operation point, a linac's beam at a PRF of 6 Hz is not so stable over time compared with clinically used beams at a PRF of 400 Hz. To overcome this problem, absorbers can be used to reduce the doserate at the detector or—in a scientific environment—the detector can be moved away from the source to a limited extend. Nevertheless, all these methods would require an additional, detector independent measurement that records the delivered doserate time dependently and correlates frames and pixel values to the actual measured dose in a specific pixel at a certain time within measurement—which is not so easy to do. Diodes, that were used to record the doserate, give the doserate in a point only. Metallic absorbers are changing the beam quality and thereby influence the EPID response to some extent in another way. Water-equivalent absorbers have to be very thick and heavy to reduce the doserate to below 5%, which is impractical.

To avoid the necessity of correlating the measured pixel response with a independently measured doserate, multi level gain correction of acquired images can also be done just by assigning a nominal doserate value (or just a number) to a specific gain image and correct a clinical image by linear interpolation between these numbers. Obviously, the resulting images are dosimetrically worthless. Nevertheless, this was practiced to provide somewhat improved image quality in clinical images.

According to the method of invention, each captured frame is correlated with the doserate measured with the monitor chamber in the linear accelerator's head directly. Alternatively, the integrating frame buffer can be correlated with an average doserate during flood field acquisition. After elimination of the beam's cross profile as described above, each pixel's response is directly related to a meaningful actual doserate that was measured accurately and simultaneously with the pixel value without further exertion.

As explained above, since the linac's doserate can be varied in discrete steps only, it is preferred to add a few additional measurement points (with special focus on very low doserates) by inserting water equivalent absorbers (PMMA plates), which absolute absorption rate has to be measured independently, e.g. with an ionization chamber in the central axis at detector distance. Their relative absorption rate can be derived in two dimensions by the primarily corrected panel itself or with the methods described above.

During flood field calibration, to overcome problems with different start up behavior of different linacs (FTM or non-FTM machines) at different prescribed doserates and energies, a timer is preferably started once the monitor chamber in the linac's head reports a certain threshold doserate (e.g. 25% of the prescribed doserate) to be exceeded. After a defined delay (e.g. 10 s), when intrabeam ghost build up has reached an equilibrium, the accumulation of frames to derive response maps for the reported doserate level will start. Typically, acquisition and averaging of about 50 frames in free running mode is sufficient to suppress vertical synchronization stripes in the resulting image, even if the panel is operated in free running mode.

Figure 13A:
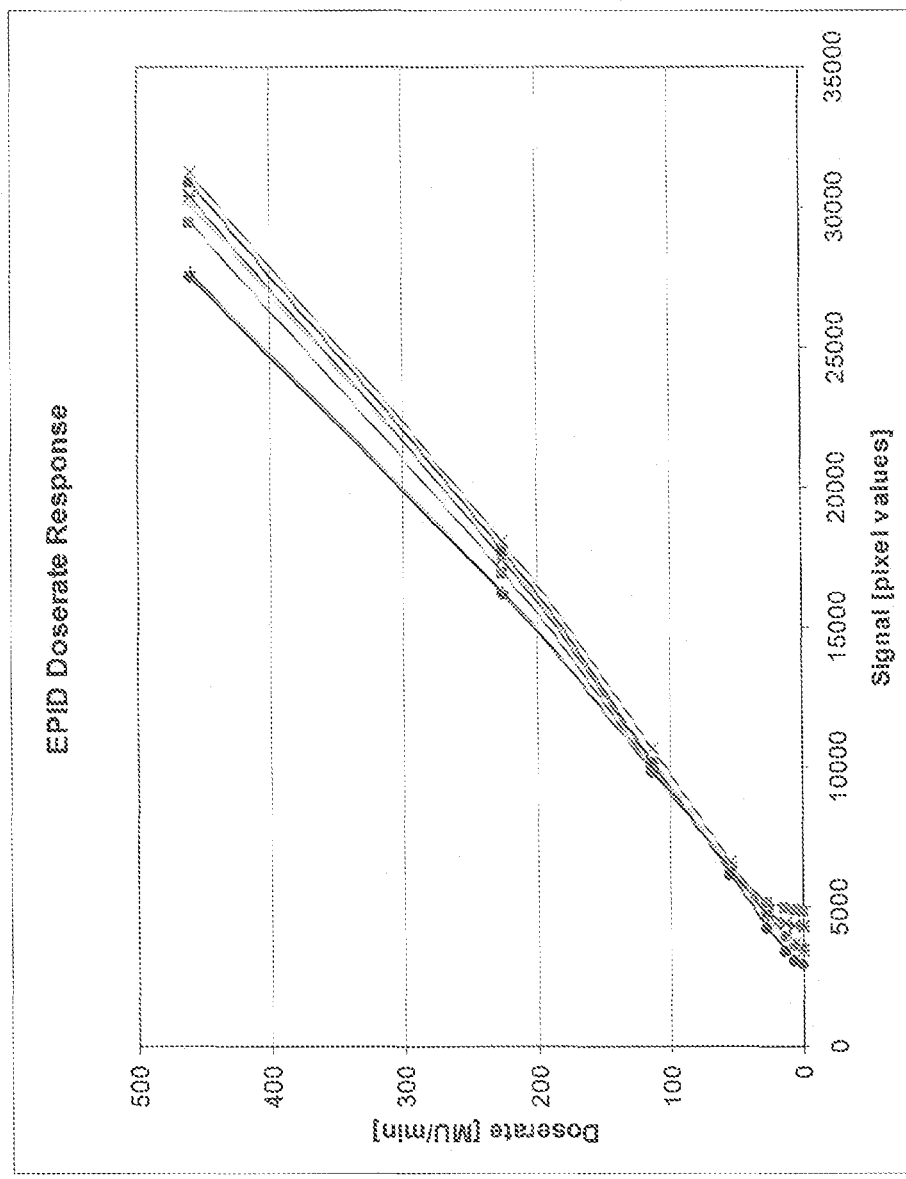
FIG. 13 shows a typical doserate response of an old panel.
Figure 13B:
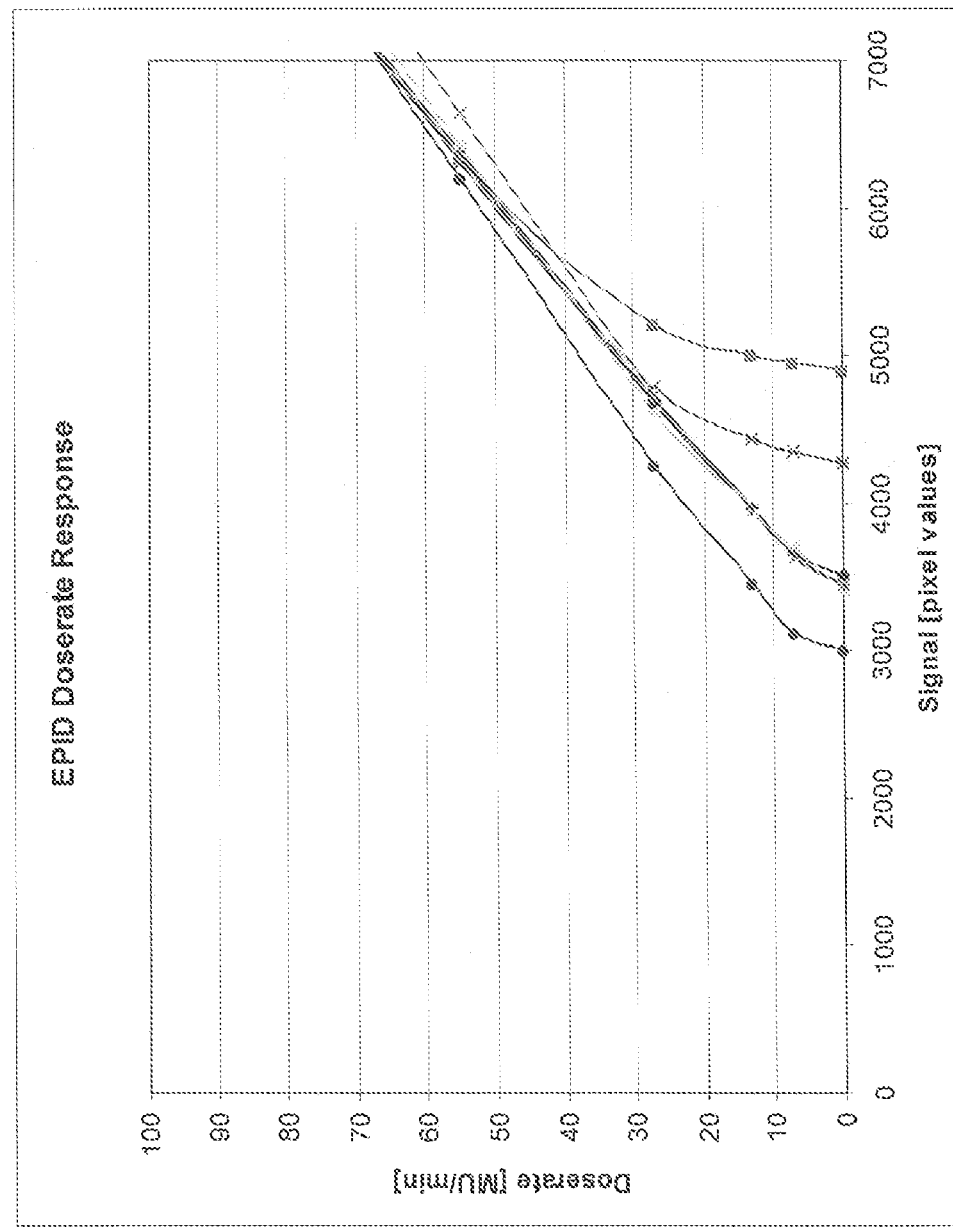
Figure 14:
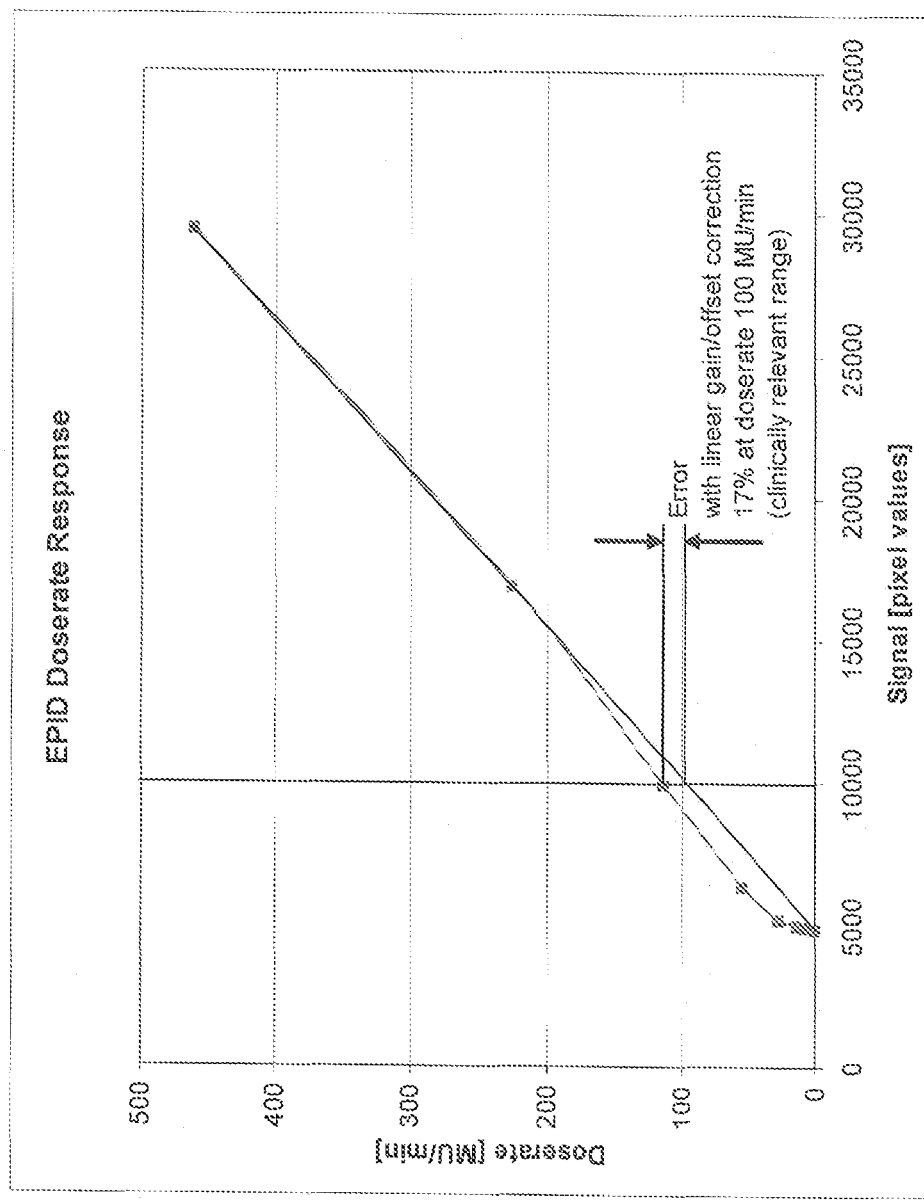
FIG. 14 shows the error associated with the assumption of a linear doserate—signal relationship.

FIG. 13 shows a typical doserate response of an old panel. As can be taken from FIG. 13a, there is a fairly linear relationship in higher doserate ranges. Slightly increasing gains for all pixels indicate higher pixel sensitivity at highest doserates compared to the middle range. However, it has been recognized by the inventor that the pixel sensitivity is significantly reduced by radiation with very low doserates in rows that show an increased offset value due to aging of the panel, as shown in FIG. 13b which is a zoom into lowest doserates of FIG. 13a. The effect is that assuming a linear relationship over the whole doserate as in the prior art results in a substantial error for lower doserates. The error under linear assumption (two point measurement gain and offset correction) is in the shown example about 17% of the doserate at flood field irradiation with 100 MU/min, as shown in FIG. 14. This effect reduces the signal to noise ratio (SNR) to below 1 in that clinically relevant range.

With increasing temperature (during the day) and with increasing age of the panel, the offset value (i.e. doserate 0) increases to higher signal values, for example in FIG. 13b from originally 3000 to up to 5000.

Therefore, although the behavior of a pixel might be fairly linear at all higher doserates, the conversion from pixel signal to doserate will not work properly if the conversion is based on a gain map that stems from a conventional two point measurement (doserate zero and maximal doserate). The error that is introduced into the gain-offset corrected image is of magnitude 2000—i.e. the difference between good and poor rows in the offset image—and disturbs clinically images on older panels too much, since, in many cases, the anatomical image information is of much lower magnitude. With newly gain-offset calibrated devices, the effect of the erroneous correction can then be seen over the total linear range, is reduced, if the gain-offset correction is turned off with the result of getting poor images at the low doserate regions. Although clinical portal imaging system typically works in doserate regions of above 100 MU/min (flood field at detector), intensity modulated radiotherapy (IMRT) is a specific task, because the image acquisition time increases due to the higher number of monitor units applied, and the integral image contribution of background and low dose regions with scatter from small segments increases. Therefore, verification of IMRT beams requires a good calibration particularly at very low doserates. Furthermore, such low doserates may occur, for example, with an image of a lateral pelvis of a heavy patient with tiny gold markers shadowed by bony structures or of wedged beams. These obstacles are now overcome with the present invention.

If a clinically or dosimetric image is acquired, the correction of the poor native image can be applied by conversion from signal to doserate corresponding to the non-linear relationship that is stored in memory in a three dimensional lookup table. Since the offset signal at the time of calibration could differ from the dynamically measured actual offset image, an additional correction must be applied: Before conversion, the native signal value of a pixel is reduced by an delta-amount, that represents the difference between the offset value of that pixel in the actual offset image and the offset value of the pixel at the time of calibration. This amount can be modified in order to remodel a change in the signal to doserate curve when the offset point in the curve is changing. Typically, the amount to correct for changes in offset image is reduced at higher signal values (i.e. higher doserates). Applying the unmodified delta-amount in the correction, a simple shift (and no deformation) of the doserate response curve would be achieved.

In a preferred embodiment of the invention, bad pixels are identified and interpolated. Bad pixels shall preferably be determined in fully corrected images only: If irradiated with a flat flood field at a given doserate, a pixel can be assumed to be bad, if the corrected image's pixel value differs from its neighborhood's median value (e.g. 20×20 pixel array) more than a certain percentage value (e.g. 0.5%). If bad pixels were defined in such a way, their absolute number over the entire detector array (margins at the borders excluded) could be an objective indicator for final replacement of very old panels. However, to that point, after applying all the corrections described above, the bad pixel map is almost empty even for our poorest 2½ year old panel.

Alternatively, instead of defining a static bad pixel map, application of a 3×3 median operator would also eliminate single bad pixels and rows without decreasing the image's spatial accuracy too much (beyond 1 pixel's width).

In a further preferred embodiment of the invention, post-processing can be applied on the measurements. Automatic window and level adjustments can be applied according to procedures utilizing histogram analysis. Digital processing filters like Unsharp Masking or others may be applied. However, there are two filters which are according to the invention preferably applied on clinical images acquired with flat panels:

If the panel is operated in free running mode, it is likely to receive (vertical) synchronization stripes in the resulting image. These stripes can be eliminated with methods similar to the ones described above for separation of offset and gain images and correction of horizontal row artifacts: regionally, the median of a part of a column can be calculated and compared with the regional medians of the neighboring columns. If the regional median is higher than the mean of the neighboring column's regional median, than the concerned pixel's value shall be reduced by a multiplicative correction to the mean value of neighbors. The correction has to be multiplicative, since it can be assumed that darker columns of higher intensity are due to multiple column read outs which were accumulated in the image. Typically, the kernel to derive the median can be of length of for example 20 pixels or more while the width of the kernel, the number of neighboring columns obeyed, should be smaller (e.g. 9 pixels) to achieve clinically useful images without synchronization stripes.

Additionally, on very poor panels or under extreme conditions, e.g. during portal imaging of electron beams, it may be useful to apply another post-processing filter to eliminate the rest of row artifacts in clinical images: Like described above in detail, row artifacts can also be eliminated from clinical images as well by applying locally limited (regional) operators to shift the median of a row concerned to the mean of neighboring row's median and thereby eliminating disturbing impressions of subpanel borders etc.

Alternatively, such filters can generally be constructed to work in the frequency domain, after performing a Fourier transformation of the image.

The substantial improvements and advantages associated with the present invention are explained in the following.

Figure 17B:
FIG. 17 shows a portal image of a hip, acquired with a two and a half year old amorphous silicon panel corrected according to conventional methods in comparison to the present invention.
Figure 17A:
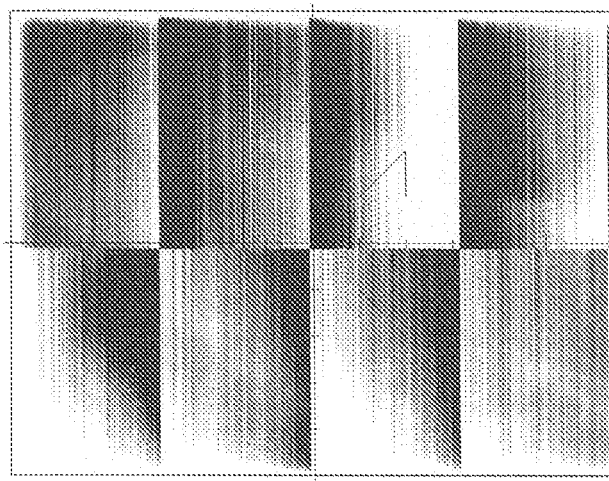

FIG. 17 shows a portal image of a hip, acquired with a two and a half year old amorphous silicon panel mounted on a linac working from 7:00 to 20:00 hours with 80 patients/100 portal images a day. FIG. 17a shows the image being newly calibrated, and having gain and dynamic offset correction applied according to conventional technology/methods. The improvement of the invention over this conventional correction method is clearly seen from a comparison with FIG. 17b. FIG. 17b shows the "repaired" image, acquired after performing the calibration and correction methods of the present invention.

Figure 18B:
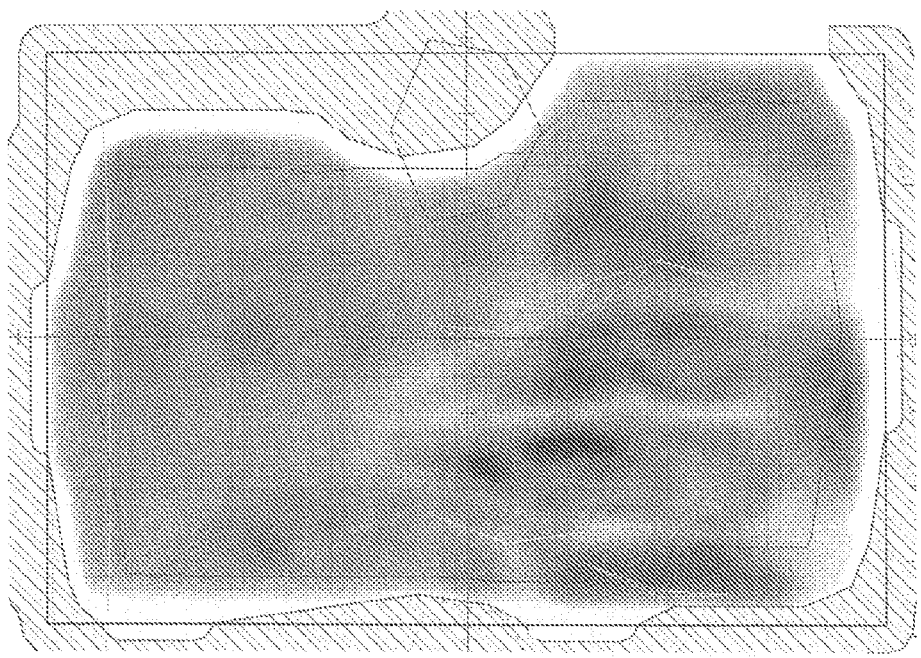
FIG. 18 shows a portal image of a ventral beam directed towards the skull/nose of a patient, acquired with the same panel of FIG. 17, corrected according to conventional methods in comparison to the present invention.
Figure 18A:
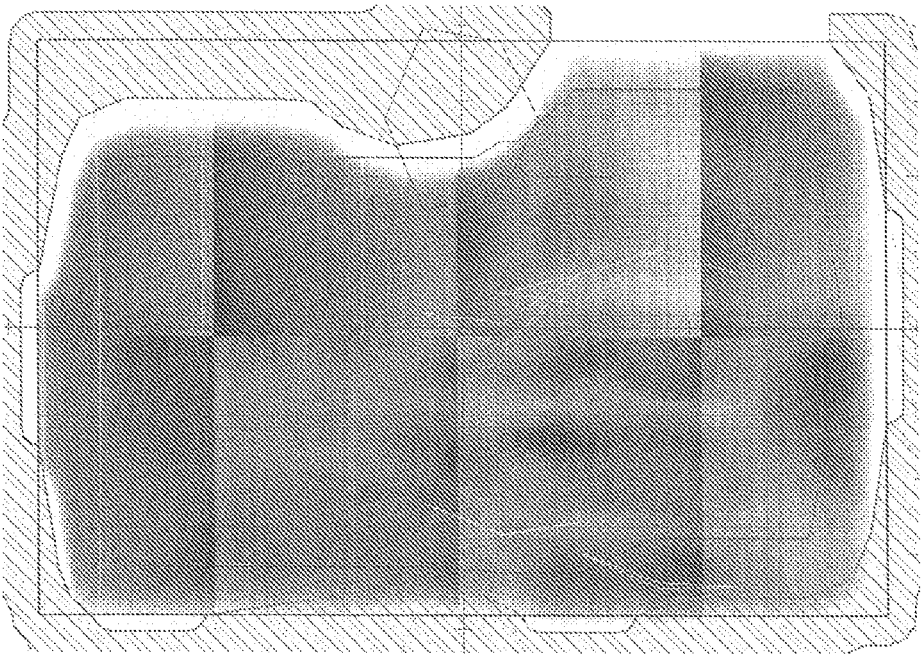

FIG. 18 shows a portal image of a ventral beam directed towards the skull/nose of a patient, acquired with the same panel of FIG. 17. Again, FIG. 18a shows the result of conventional corrections (linear gain offset), and FIG. 18b the improved image according to the invention with full dynamic range and significantly improved signal to noise ratio.

Figure 19A:
FIG. 19 shows portal images of a lateral head and neck patient, corrected according to conventional methods in comparison to the present invention.
Figure 19B:
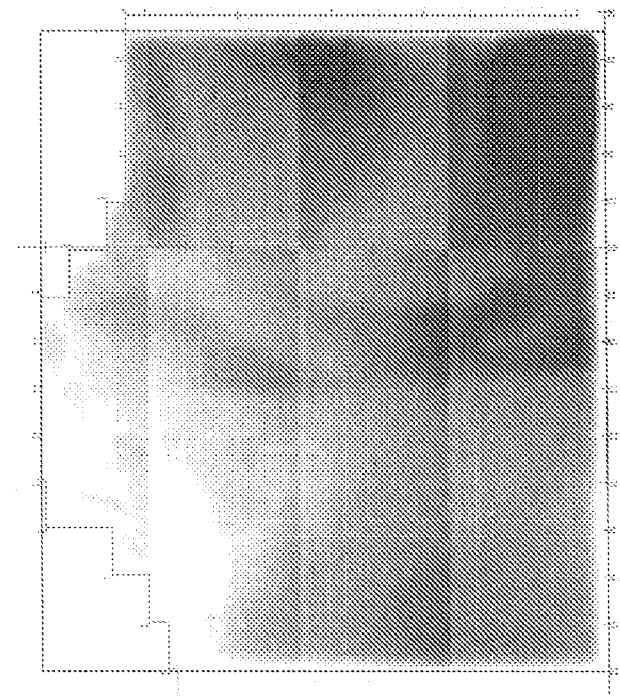

FIG. 19 shows portal images of a lateral head and neck patient, again acquired with the same panel. FIG. 19a shows the result of conventional corrections (linear gain offset), and FIG. 18b the improved image according to the invention with full dynamic range and significantly improved signal to noise ratio.

As shown with FIG. 20, automatic registration of images allows an immediate overlay of beam's aperture and internal patient structures: The position of gold marks on treatment of the prostate (ventral and lateral view, laterally with two segments and an intersegmental collimator rotation to smoothen the penumbra) can easily be verified after the appropriate corrections have been performed all-automatically.

Figure 21B:
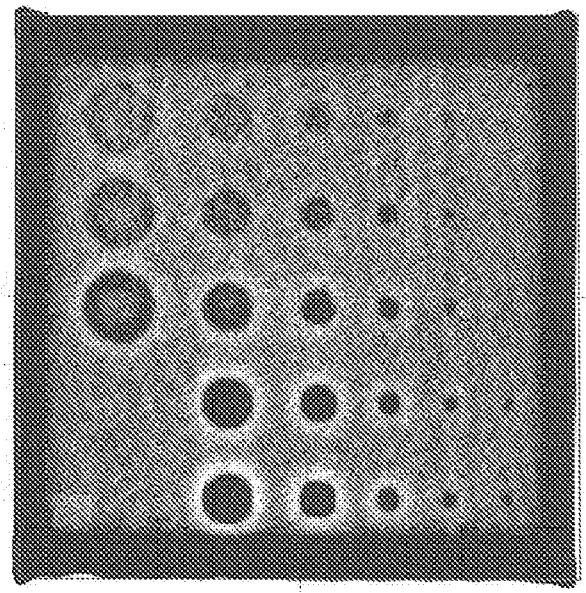
FIG. 21 shows portal images of a Las Vegas phantom after applying the corrections according to the invention.
Figure 21A:
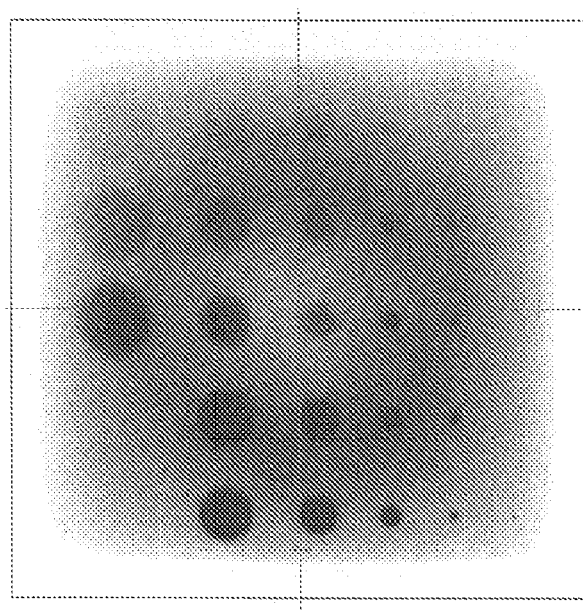

As another example, FIG. 21 shows portal images of a Las Vegas phantom after applying the corrections, acquired with the same 2½ year old panel. In FIG. 21a, absolute dose (showing a slight minimum in the centre of the field due to the beam's flatness) are shown, and FIG. 21b shows the image after post processing with an unsharp masking filter. Definitely, the old panel being used with the methods of the present invention meets the requirements.

Figure 15B:
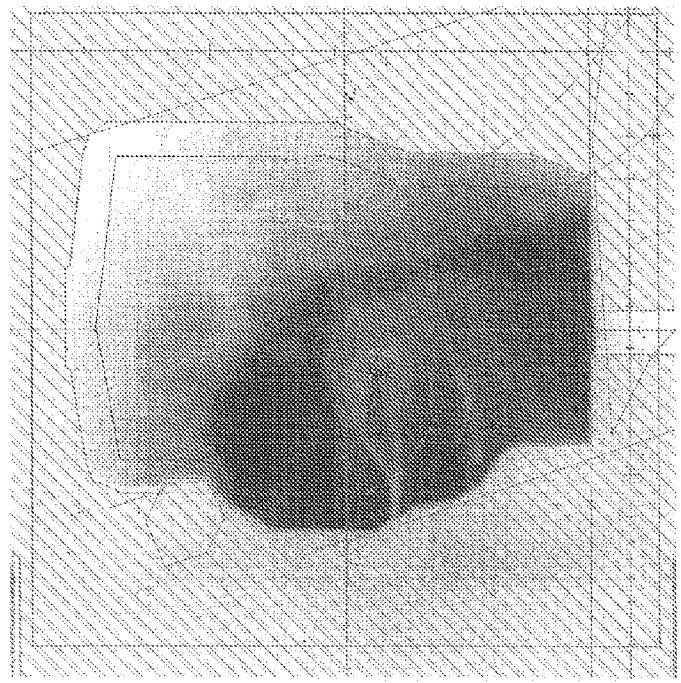
FIG. 15 shows an example relating to irradiation with electron beams.
Figure 15A:
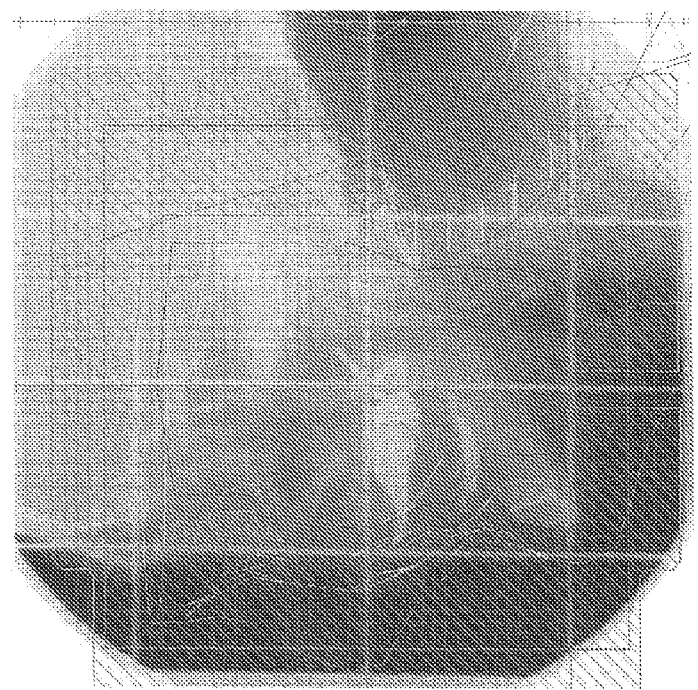

FIG. 15 shows a somewhat different example. The previous examples relate to irradiation with photon beams. Photon beams are due to their high penetration depth particularly suitable for imaging procedures. Less preferred are electron beams due to their small penetration depth. Electron beams are however accompanied by photon contamination which is typically 1-3% of the electron dose. The example of FIG. 15 shows that using the methods of the invention even with such very low photon doserates acceptable results are obtained. As shown, the mere photon contamination of electron beams can be used to acquire clinically useful images without further modification of frame integration time or changes in calibration to verify irregularly shaped electron end frames directly. FIG. 15a shows a simulator image, and FIG. 15b shows a portal image from 80 MU of 8 MeV electron beam.

Those in the art will appreciate that various adaptations and modifications of the above-described embodiments can be configured without departing from the scope and spirit of the invention. Also, embodiments of the present invention may differ from the description of process steps of the invention. In addition, the particular arrangement of the process steps is not meant to imply a fixed order to the steps; embodiments of the present invention can be practiced in any order that is practicable. Therefore, it is to be understood that, within the scope of the appended claims, the invention may be practiced other than as specifically described herein.

The invention claimed is:

1. A method of estimating an offset image of an unused imaging device from an offset image of said imaging device already aged, comprising:

a. calculating the median value of all pixels in each row of an imaging device already aged;

b. determining the minimum value of all medians of all rows of the imaging device already aged; and
c. subtracting the difference of each rows median and the minimum median of all rows from each pixel in each row to receive a first estimation of the offset image of the unused imaging device;
d. calculating the standard deviation of all pixels in each row which values are within a certain range related to the row's median value;
e. determining the maximal standard deviation of all pixels which values are within a certain range related to the row's median value from such rows of lowest medians; and
f. amplifying texture information along each row by dividing the difference of each pixel's value to the mean value of the pixel's neighborhood in the row by the ratio of standard deviations calculated in (d) and the maximal standard deviation as determined in (e) to receive a better estimation of the offset image of the unused imaging device.

2. The method of claim 1, wherein the imaging device is a panel consisting of various sub-panels.

3. The method of claim 2, wherein steps (a) and (c) and optionally (d) and (f) are performed for each sub-panel.

4. A method of image correction comprising the steps of
a. subtracting the offset image as derived in claim 1 from a native image; and
b. multiplying the difference with a gain image.

5. A system for image correction comprising:
means for calculating the median value of all pixels in each row of an aged imaging device;
means for determining the minimum value of all medians of all rows of the aged imaging device;
means for calculating, for each row, the difference between the median value of each row and the minimum value of all medians;
means for setting the difference as a disturbing part of an aged offset image; and
means for subtracting the difference from a target image obtained with the aged imaging device.

* * * * *